US009381383B2

(12) United States Patent
Lucet-Levannier et al.

(10) Patent No.: US 9,381,383 B2
(45) Date of Patent: Jul. 5, 2016

(54) PHOTOPROTECTIVE COMPOSITIONS AND FILMS, AND A PREPARATION METHOD

(75) Inventors: Karine Lucet-Levannier, Rueil-Malmaison (FR); Jean-Thierry Simonnet, Cachan (FR); Bertrand Lion, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/502,291

(22) PCT Filed: Oct. 21, 2010

(86) PCT No.: PCT/IB2010/054778
§ 371 (c)(1),
(2), (4) Date: Jun. 11, 2012

(87) PCT Pub. No.: WO2011/048570
PCT Pub. Date: Apr. 28, 2011

(65) Prior Publication Data
US 2012/0282310 A1    Nov. 8, 2012

Related U.S. Application Data

(60) Provisional application No. 61/261,135, filed on Nov. 13, 2009, provisional application No. 61/261,056, filed on Nov. 13, 2009, provisional application No. 61/261,107, filed on Nov. 13, 2009, provisional application No. 61/261,091, filed on Nov. 13, 2009.

(30) Foreign Application Priority Data

Oct. 22, 2009   (FR) ..................... 09 57439
Oct. 22, 2009   (FR) ..................... 09 57440
Oct. 22, 2009   (FR) ..................... 09 57441
Oct. 22, 2009   (FR) ..................... 09 57442
May 6, 2010    (FR) ..................... 10 53529
May 6, 2010    (FR) ..................... 10 53535
May 6, 2010    (FR) ..................... 10 53539
May 6, 2010    (FR) ..................... 10 53541

(51) Int. Cl.
*A61K 8/72*     (2006.01)
*A61K 8/02*     (2006.01)
*A61Q 19/00*    (2006.01)
*A61Q 17/04*    (2006.01)
*G02B 5/28*     (2006.01)
*A61K 8/25*     (2006.01)
*A61K 8/90*     (2006.01)

(52) U.S. Cl.
CPC .............. *A61Q 17/04* (2013.01); *A61K 8/0266* (2013.01); *A61K 8/25* (2013.01); *A61K 8/90* (2013.01); *G02B 5/28* (2013.01); *G02B 5/283* (2013.01); *G02B 5/285* (2013.01); *G02B 5/286* (2013.01); *G02B 5/287* (2013.01); *A61K 2800/412* (2013.01); *A61K 2800/436* (2013.01); *A61K 2800/437* (2013.01); *A61K 2800/654* (2013.01)

(58) Field of Classification Search
None
See application file for complete search history.

(56) References Cited

U.S. PATENT DOCUMENTS

| | | |
|---|---|---|
| 2,463,264 A | 3/1949 | Graenacher et al. |
| 5,166,355 A | 11/1992 | Leistner et al. |
| 5,237,071 A | 8/1993 | Leistner et al. |
| 5,412,004 A | 5/1995 | Tachibana et al. |
| 5,624,663 A | 4/1997 | Deflandre et al. |
| 5,811,487 A | 9/1998 | Schulz, Jr. et al. |
| 6,225,467 B1 | 5/2001 | Esteghamatian et al. |
| 6,716,475 B1 | 4/2004 | Fink et al. |
| 6,894,086 B2 | 5/2005 | Munro et al. |
| 2002/0024163 A1 | 2/2002 | Fu et al. |
| 2003/0116062 A1 | 6/2003 | Anselmann et al. |
| 2003/0148088 A1 | 8/2003 | Padmanabhan et al. |
| 2004/0105826 A1 | 6/2004 | Soane et al. |
| 2005/0249763 A1 | 11/2005 | Legendre et al. |
| 2006/0002875 A1 | 1/2006 | Winkler et al. |
| 2008/0089917 A1* | 4/2008 | Dumousseaux et al. ...... 424/401 |
| 2008/0268002 A1 | 10/2008 | Dumousseaux et al. |
| 2008/0315270 A1* | 12/2008 | Marsh et al. .................. 257/292 |
| 2009/0041695 A1 | 2/2009 | Dumousseaux et al. |
| 2009/0041696 A1 | 2/2009 | Dumousseaux |
| 2009/0086208 A1 | 4/2009 | Kang et al. |
| 2009/0110650 A1 | 4/2009 | Candau |
| 2009/0117160 A1 | 5/2009 | Dumousseaux et al. |
| 2009/0186055 A1 | 7/2009 | Dumousseaux et al. |
| 2009/0258072 A1 | 10/2009 | Schlossman et al. |

FOREIGN PATENT DOCUMENTS

| | | |
|---|---|---|
| DE | 197 26 184 A1 | 12/1998 |
| DE | 197 46 654 A1 | 2/1999 |
| DE | 197 55 649 A1 | 6/1999 |
| DE | 198 55 649 A1 | 6/2000 |

(Continued)

OTHER PUBLICATIONS

Sally Lou, Commercial Application of Block Copolymer Photonic Gels, 2008, Massachusetts Institute of Technology, Thesis, p. 23-24 43-44, Abstract.*

(Continued)

*Primary Examiner* — Kevin S. Orwig
*Assistant Examiner* — Ping Cao
(74) *Attorney, Agent, or Firm* — Oliff PLC

(57) ABSTRACT

A photoprotective composition, in particular a cosmetic composition, that includes particles of photonic material having a polymeric multilayer interference structure, where at least two layers of the structure contain an amphiphilic polymer.

11 Claims, 2 Drawing Sheets

(56) References Cited

FOREIGN PATENT DOCUMENTS

Figure 1:
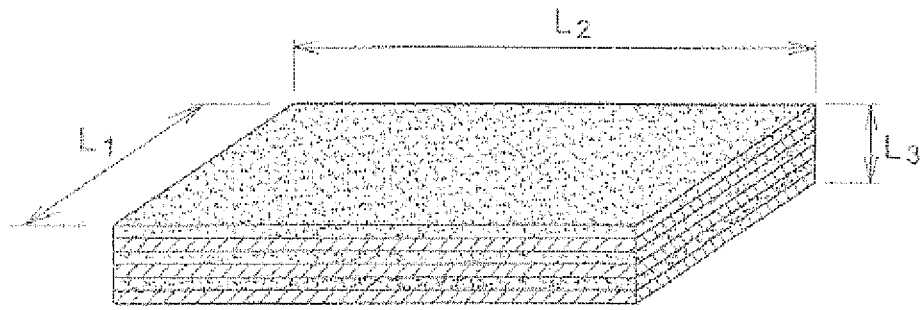

| | | |
|---|---|---|
| EP | 0 133 981 A2 | 3/1985 |
| EP | 0 669 323 A1 | 8/1995 |
| EP | 0 832 642 A2 | 4/1998 |
| EP | 0 893 119 A1 | 1/1999 |
| EP | 0 967 200 A1 | 12/1999 |
| EP | 1 008 586 A1 | 6/2000 |
| EP | 1 027 883 A2 | 8/2000 |
| EP | 1 133 980 A2 | 9/2001 |
| EP | 1 300 137 A2 | 4/2003 |
| EP | 1 411 069 A2 | 4/2004 |
| EP | 1 736 137 A1 | 12/2006 |
| FR | 2 833 487 A1 | 6/2003 |
| FR | 2 848 428 A1 | 6/2004 |
| FR | 2 851 915 A1 | 9/2004 |
| FR | 2 888 491 A1 | 1/2007 |
| FR | 2 902 647 A1 | 12/2007 |
| FR | 2 910 286 A1 | 6/2008 |
| FR | 2 921 559 A1 | 4/2009 |
| GB | 2 303 549 A | 2/1997 |
| JP | A-11-021223 | 1/1999 |
| JP | A 2006-036836 | 2/2006 |
| JP | A-2007-182392 | 7/2007 |
| JP | A-2008-239588 | 10/2008 |
| WO | WO 93/04665 A1 | 3/1993 |
| WO | WO 99/47570 A1 | 9/1999 |
| WO | WO 2004/006878 A1 | 1/2004 |
| WO | WO 2004/028488 A2 | 4/2004 |
| WO | WO 2004/055081 A2 | 7/2004 |
| WO | WO 2004/085412 A2 | 10/2004 |
| WO | WO 2005/058269 A1 | 6/2005 |
| WO | WO 2006/032741 A1 | 3/2006 |
| WO | WO 2006/034982 A1 | 4/2006 |
| WO | WO 2006/034985 A1 | 4/2006 |
| WO | WO 2006/034991 A1 | 4/2006 |
| WO | WO 2006/034992 A1 | 4/2006 |
| WO | WO 2006/035000 A1 | 4/2006 |
| WO | WO 2006/035007 A1 | 4/2006 |
| WO | WO 2006/116567 A2 | 11/2006 |
| WO | WO 2006/136719 A1 | 12/2006 |
| WO | WO 2006/136724 A2 | 12/2006 |
| WO | WO2007007283 * 1/2007 ............. A61Q 17/04 | |
| WO | WO 2007/082061 A2 | 7/2007 |
| WO | WO 2008/007267 A2 | 1/2008 |
| WO | WO 2009/061473 A2 | 5/2009 |
| WO | WO 2011/045746 A2 | 4/2011 |

OTHER PUBLICATIONS

Forster et al., Amphiphilic block copolymers in structure controlled nanomaterial hybrids, Adv. Mater., 1998, vol. 10, pp. 195-217.*

Kang et al., "Broad-wavelength-range chemically tunable block-copolymer photonic gels," Nature Materials, vol. 6, pp. 957-960, Dec. 2007.

Kang et al., "Full Color Stop Bands in Hybrid Organic/Inorganic Block Copolymer Photonic Gels by Swelling-Freezing," Journal of American Chemical Society, vol. 131, pp. 7538-7539, 2009.

Diffey et al., "A new substrate to measure sunscreen protection factors throughout the ultraviolet spectrum," J. Soc. Cosmet. Chem., vol. 40, pp. 127-133, May/Jun. 1989.

Wang et al., "A facile method of shielding from UV damage by polymer photonic crystals," Polymer International, vol. 57, pp. 509-514, 2008.

Schroden et al., "Optical Properties of Inverse Opal Photonic Crystals," Chem. Mater., vol. 14, pp. 3305-3315, 2002.

Kim et al., "Microwave-Assisted Self-Organization of Colloidal Particles in Confining Aqueous Droplets," Journal of American Chemical Society, vol. 128, pp. 10897-10904, 2006.

Hong et al., "Fabrication of Spherical Colloidal Crystals Using Electrospray," Langmuir, vol. 21, pp. 10416-10421, 2005.

Li et al., "Ordered macroporous titania photonic balls by micrometer-scale spherical assembly templating," Journal of Materials Chemistry, vol. 15, pp. 2551-2556, 2005.

Klein et al., "Synthesis of Spherical Polymer and Titania Photonic Crystallites," Langmuir, vol. 21, pp. 6669-6674, 2005.

Kim et al., "Optofluidic Synthesis of Electroresponsive Photonic Janus Balls with Isotropic Structural Colors," Advanced Materials, vol. 20, pp. 4129-4134, 2008.

Klein et al., "Preparation of monodisperse PMMA microspheres in nonpolar solvents by dispersion polymerization with a macromonomeric stabilizer," Colloid. Polym. Sci., vol. 282, pp. 7-13, 2003.

Wang et al., "Effects of fabrication conditions on the characteristics of etanidazole spray-dried microspheres," J. Microencapsulation, vol. 19, No. 4, pp. 495-510, 2002.

Kim et al., "Patterned Colloidal Photonic Domes and Balls Derived from Viscous Photocurable Suspensions," Advanced Materials, vol. 20, pp. 3211-3217, 2008.

Schlossman, "Treated Pigments: New Ways to Impart Color on the Skin," Cosmetics & Toiletries, vol. 105, pp. 53-64, Feb. 1990.

Nov. 15, 2011 International Search Report issued in Application No. PCT/IB2010/054609.

Nov. 15, 2011 Written Opinion of the International Searching Authority issued in Application No. PCT/IB2010/054609 (with translation).

Dec. 27, 2011 International Search Report issued in Application No. PCT/IB2010/054778.

Dec. 27, 2011 Written Opinion of the International Searching Authority issued in Application No. PCT/IB2010/054778.

U.S. Appl. No. 13/500,036, filed May 16, 2012 in the name of Jean-Thierry Simonnet et al.

U.S. Office Action dated Dec. 31, 2013 from U.S. Appl. No. 13/500,036.

Japanese Office Action dated Nov. 6, 2014 from Japanese Application No. 2012-534816.

Apr. 30, 2015 Office Action issued in U.S. Appl. No. 13/500,036.

* cited by examiner

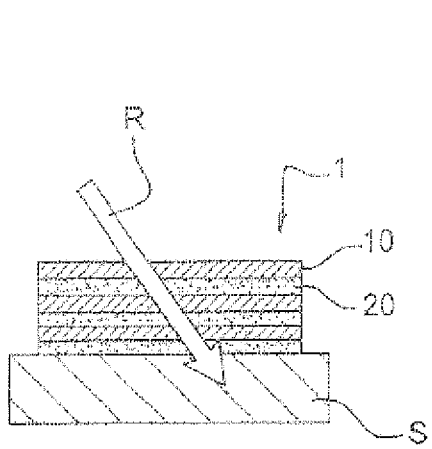
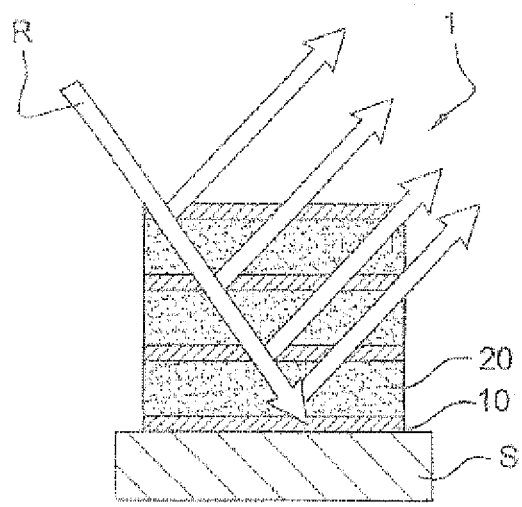
Fig. 3
Fig. 4
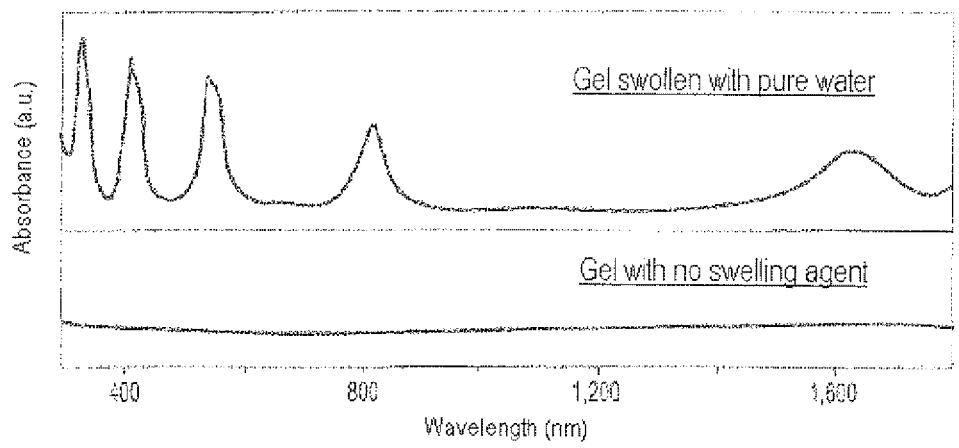
Fig. 5

PHOTOPROTECTIVE COMPOSITIONS AND FILMS, AND A PREPARATION METHOD

The present invention relates to compositions and to methods for photoprotecting various materials using particles of photonic material, in particular particles having a polymeric multilayer interference structure obtained from photonic gels.

Furthermore, the present invention relates to compositions and to methods of treating human keratinous material.

PRIOR ART

Current photoprotective compositions use combinations of various screening agents, especially soluble or insoluble organic screens. The absorption spectrum of each of said screens is rarely broad enough to cover the whole UV spectrum, and combinations are necessary.

Further, a large number of soluble organic screens may cause compatibility problems with the ingredients usually contained in them, especially as a result of interactions with other organic screens or with active molecules such as antioxidants or vitamins, and their photostability may not be entirely satisfactory. Many patents are concerned with solving this problem—an indication that this problem crops up repeatedly.

Many non-cosmetic industry sectors also use UV screens to photoprotect various materials against the effects of UV radiation, in particular solar radiation.

This is particularly true of paint, ink, or protective coating formulations for applying to substances that are permanently exposed to UV radiation, such as construction materials, materials used in the automobile industry, or plastics packaging materials. In particular, UV screens are being developed for colorant formulations that need to be transparent, photostable, compatible with the usual ingredients contained in said formulations, and effective in providing the looked-for color with resistance to light.

Similar considerations apply with polymer compositions used in particular in the manufacture of plastics materials that are stable on storage; they need UV light screens to be developed that are particularly adapted to the methods of manufacturing and transforming polymers, and in particular they need to be able to tolerate the high temperatures used in extrusion.

In the natural fiber and/or artificial fiber and/or synthetic fiber industry, broad spectrum photostable UV screens are being developed that are compatible with methods of manufacturing said fibers, in particular in the context of the manufacture of fibers made of polyamide such as nylon, which are resistant to high temperatures and can incorporate UV protection during extrusion. Further, UV screens are being developed that have good affinity, good adhesion to fibers, and thus in particular can provide good resistance upon frequent washing. The UV screens being developed must also provide both good protection of the textile fibers and also of the skin and other human keratinous material in contact with said fibers.

The mineral or organic glass industry, in particular for glass used in ophthalmology, is developing UV screens that need to have a broad spectrum (active in the WA and in the UVB regions), and that are photostable, transparent, and compatible with the various techniques for treating glass, such as methods of keying onto the glass matrix or applying a photoprotective coating, for example with polycarbonate glass.

Interference materials constituted by a multilayer structure may be used as screening agents. With films having a polymeric multilayer interference structure, the layers may number up to several hundred, for example.

Such films may be produced by extrusion, are usually transparent, and are several hundred μm [micrometer] thick.

The use of a metal layer, for example of $TiO_2$ or ZnO, can produce greater differences in refractive index and can reduce the number of layers constituting the film. However, films using that technology may become opaque to visible light and may also prove to be fairly rigid.

In a variation, when the films are thick and have a large number of layers, their efficiency may be significantly reduced when they are fragmented into particles. Because of the great thickness of the films, "edge effects" may very substantially reduce the production of interference.

The use of holographic pigments in order to produce a reflection in the UV spectrum is known from application FR 2 921 559.

Application FR 2 888 491 discloses a photoprotective composition comprising a screening agent having a multilayer interference structure, the screening agent comprising alternating high refractive index layers and low refractive index layers.

"Photonic materials" or "photonic crystals" are known from application US 2009/0086208 that are constituted by a periodic arrangement of at least two polymeric portions having different dielectric constants. In particular, those polymeric photonic materials contain at least one polymeric portion that is capable, under the influence of an altering stimulus, of producing a change in at least one physical, chemical, or dielectric characteristic including the dimension, shape, dielectric constant, refractive index, color, or other parameter. That change results in modifying a wavelength of electromagnetic radiation diffracted by the photonic material.

A photonic gel is a film having a polymeric multilayer structure that may comprise a block polymer that spontaneously forms a periodic lamellar structure during deposition onto a support. Such a material may have interference properties, for example when it is brought into contact with a swelling agent.

Photonic gels are known from publications by E. Thomas: Nat Mat Vol 6, 957-960, 2008 and J Am Chem Soc 2009, 131, 7538-7539.

There is a need to benefit from novel UV light screening systems adapted to photoprotecting materials such as those mentioned above.

There is a need to benefit from non-soluble screening materials that can be used to cover the UVA and/or UVB spectrum, that are completely harmless, inert as regards the environment, are photostable and not photoreactive, that do not have compatibility problems with the other constituents of the compositions containing them, and that do not modify the mechanical properties of the materials of packaging materials in a negative manner.

There is a need to benefit from coloring effect materials that are completely harmless, inert as regards the environment, photostable, and not photoreactive, that do not have compatibility problems with the other constituents of the compositions containing them, and that do not modify the mechanical properties of packaging materials in a negative manner.

There is also a need to have available polymeric films with a multi-portion structure, in particular having a polymeric multilayer interference structure, with optical properties that are only slightly affected or are unaffected when they are fragmented into particles.

The invention, which is intended to satisfy some or all of the needs mentioned above, provides the use of particles of photonic material, in particular particles having a polymeric multilayer interference structure obtained from photonic materials, in particular photonic gels.

SUMMARY

"Photoprotective" Application
Photoprotective Compositions and Films

In first exemplary embodiments the invention provides a photoprotective composition, in particular a cosmetic, including particles of photonic material.

The particles of photonic material may in particular be particles having a polymeric multilayer interference structure with at least two layers comprising a polymer. Said polymer may be an amphiphilic polymer defining at least two layers of said structure. In other words, at least two layers of said structure may be formed by an amphiphilic polymer.

In the context of the invention, the term "photoprotective composition" is used to mean a composition that is capable of protecting any material, in particular human keratinous materials, against UV radiation. In particular it has a transmission factor, measured before application to said material, that is less than or equal to 70%, 60%, 50%, 40%, 30%, 20%, 10%, 5%, or even more preferably less than or equal to 1%, for at least one wavelength in the range 250 nm to 400 nm, more preferably over the whole of said range. Screening is much better when the transmission factor over the range 250 nm to 400 nm is low.

In the context of the invention, the term "photonic material" is used for a polymeric material comprising a plurality of different portions arranged in a periodic manner, capable of interfering with electromagnetic radiation and of modifying it, with at least a first and a second portion each having a respective dielectric constant and a respective ability to modify the electromagnetic radiation dimensionally by at least 5 nm such that the portions define a ratio of dielectric constants of at least 1 for a continuous wavelength range from 10 nm to 10 micrometers when subjected to an altering stimulus.

In the context of the invention, the term "polymeric multilayer interference structure" is used for a stack of at least two layers of polymer, preferably more than two layers, the stack being capable of producing interference, for example in order to screen UV, and for example to provide protection against UVA, thereby limiting browning of the skin, and/or to produce a color and/or to lighten the complexion and/or to modify the spectral reflectance, depending on the application.

The interference may provide the polymeric multilayer interference structure with a transmission spectrum including one or more transmission minima or a reflection spectrum including one or more reflection peaks in the wavelength range 250 nm to 800 nm.

The term "amphiphilic polymer" should be understood to mean a polymer comprising a hydrophilic group and a hydrophobic group. An amphiphilic polymer may, for example, be a block copolymer comprising at least one hydrophilic block and at least one hydrophobic block.

According to other exemplary embodiments the invention provides a composition, in particular a cosmetic composition, including particles of photonic material, in particular particles having a polymeric multilayer interference structure, comprising a polymer having a UV screen within it. The polymer is, for example, an amphiphilic polymer, for example as defined above.

The term "polymer having a UV screen within it" should be understood to mean that particles having UV screening properties and that are distinct from the groups forming said polymer are imprisoned in the structure formed by said polymer. In other words, the UV screen is present in addition to said polymer in the structure formed thereby.

According to other exemplary embodiments the invention provides a film that photoprotects against solar UV radiation, for application to a material, in particular to human keratinous materials, the film including a photonic material, in particular a multilayer interference structure screening solar UV radiation, in which at least two layers comprise an amphiphilic polymer.

The amphiphilic polymer may define at least two layers of the polymeric multilayer interference structure screening solar UV radiation. In other words, as with the particles, at least two layers of the structure may be formed by an amphiphilic polymer.

According to other exemplary embodiments the invention provides a photoprotective film for application to a material, in particular to human keratinous materials, comprising a photonic material, more particularly a polymeric multilayer interference structure, comprising a polymer having a UV screen within it for example as defined above.

The photoprotective films described above may be applied to a material, for example selected from materials manufactured from at least one synthetic or natural polymer, organic or mineral glasses, and materials comprising at least natural fibers and/or artificial fibers and/or synthetic fibers such as textiles or papers.

The formulations for the photoprotective films are selected in such a manner that they have a transmission factor, measured before application to the material of interest, in particular to keratinous materials, that is less than or equal to 70%, 60%, 50%, 40%, 30%, 20%, 10%, 5%, or even better preferably less than or equal to 1%, for at least one wavelength in the range 250 nm to 400 nm, more preferably over the whole of said range. Screening is even better when the transmission factor over the range 250 nm to 400 nm is low.

Preparation Methods

In other exemplary embodiments, the invention provides a method of preparing a photoprotective composition as described above, said method comprising:

a) a step of bringing a swelling agent into contact with a photonic material, in particular having a Polymeric multilayer structure with at least two layers comprising an amphiphilic polymer;

b) a step of fragmenting a film of photonic material, in particular a film having a polymeric multilayer structure in which at least two layers comprise an amphiphilic polymer, into particles of photonic material, in particular into particles having a polymeric multilayer structure with a largest dimension of 100 μm or less and/or with a smallest dimension of 100 nm or more; and c) a step of dispersing the particles of photonic material, in particular particles having a polymeric multilayer interference structure obtained after carrying out steps a) and b), in a suitable medium;

step b) being carried out before or after step a).

According to other exemplary embodiments, the invention provides a method of preparing a photoprotective composition as described above, said method comprising:

a) a step of bringing a swelling agent including a dissolved UV screen into contact with a photonic material, in particular a photonic material having a polymeric multilayer structure;

b) a step of fragmenting a film of photonic material, in particular a film having a polymeric multilayer structure, into particles of photonic material, in particular into particles having a polymeric multilayer structure with a largest dimension of 100 µm or less and/or with a smallest dimension of 100 nm or more; and c) a step of dispersing the particles of photonic material, in particular particles having a polymeric multilayer interference structure obtained after carrying out steps a) and b), in a suitable medium;

step b) being carried out before or after step a).

The photoprotective compositions prepared by the methods described above may be photoprotective and cosmetic compositions, the dispersion of step c) then being carried out in a cosmetically acceptable medium.

Uses of Photoprotective Compositions and Films

According to other exemplary embodiments the invention provides a method of photoprotecting a material against solar UV radiation, the method comprising the steps consisting in:

treating said material with a photoprotective composition including particles of photonic material, more particularly particles having a polymeric multilayer interference structure, at least two layers of said structure comprising an amphiphilic polymer; or integrating at least said composition into said material According to other exemplary embodiments the invention provides a non-therapeutic and in particular a cosmetic method of photoprotecting human keratinous materials against solar UV radiation, the method comprising the step consisting in applying to the human keratinous materials a photoprotective cosmetic composition including particles of photonic material, more particularly particles having a polymeric multilayer interference structure, at least two layers of said structure comprising an amphiphilic polymer.

Other exemplary embodiments of the invention also provide a physiologically acceptable, in particular a cosmetic composition, for use in a method of photoprotection of human keratinous material against solar UV radiation, in particular in a method for reducing the risk of apparition of a skin cancer, Wherein said composition includes particles of photonic material, more particularly particles having a polymeric multilayer interference structure, at least two layers of said structure comprising an amphiphilic polymer. Unless, otherwise specified, said composition may present all the features of the cosmetic compositions according to the present invention.

According to other exemplary embodiments the invention provides a method of photoprotecting an ink, a paint, or a coating, the method comprising the step of incorporating into said ink or said paint or said coating at least one composition including particles of photonic material, more particularly particles having a polymeric multilayer interference structure, at least two layers of said structure comprising an amphiphilic polymer.

According to other exemplary embodiments the invention provides a method of photoprotecting a material manufactured from at least one synthetic or natural polymer, the method comprising the step of:

treating said polymer with a composition including particles of photonic material, more particularly particles having a polymeric multilayer interference structure, at least two layers of said structure comprising an amphiphilic polymer; or integrating said composition into said material.

According to other exemplary embodiments the invention provides a method of photoprotecting an organic or mineral glass comprising the step of:

treating said glass with at least one composition including particles of photonic material, more particularly particles having a polymeric multilayer interference structure, at least two layers of said structure comprising an amphiphilic polymer; or integrating said composition into said glass.

According to other exemplary embodiments the invention provides a method of photoprotecting a material comprising at least natural fibers and/or artificial fibers and/or synthetic fibers such as textiles or papers, the method comprising the step of:

treating said material with at least one composition including particles of photonic material, more particularly particles having a polymeric multilayer interference structure, at least two layers of said structure comprising an amphiphilic polymer; or integrating said composition into said material.

According to other exemplary embodiments the invention provides a method of photoprotecting a material against solar UV radiation, the method comprising the step consisting of:

treating said material with a photoprotective composition including particles of photonic material, more particularly particles having a polymeric multilayer interference structure, comprising a polymer having a UV screen within it, for example an amphiphilic polymer as defined above; or integrating at least said composition into said material.

According to other exemplary embodiments the invention provides a non-therapeutic, and in particular a cosmetic, method of photoprotecting human keratinous materials against solar UV radiation, the method comprising the step consisting in applying to human keratinous materials a photoprotective cosmetic composition including particles of photonic material, more particularly particles having a polymeric multilayer interference structure, comprising a polymer having a UV screen within it, for example an amphiphilic polymer as defined above.

Other exemplary embodiments of the invention also provide a physiologically acceptable, in particular a cosmetic composition, for use in a method of photoprotection of human keratinous material against solar UV radiation, in particular in a method for reducing the risk of apparition of a skin cancer, Wherein said composition particles of photonic material, more particularly particles having a polymeric multilayer interference structure, comprising a polymer having a UV screen within it, for example an amphiphilic polymer as defined above.

Unless, otherwise specified, said composition may present all the features of the cosmetic compositions according to the present invention.

According to other exemplary embodiments the invention provides a method of photoprotecting an ink, a paint or a coating, the method comprising the step of incorporating into said ink or paint or said coating at least one composition including particles of photonic material, more particularly particles having a polymeric multilayer interference structure, comprising a polymer having a UV screen within it, for example an amphiphilic polymer as defined above.

According to other exemplary embodiments the invention provides a method of photoprotecting a material manufactured from at least one synthetic or natural polymer, the method comprising the step of:

treating said polymer with a composition including particles of photonic material, more particularly particles having a polymeric multilayer interference structure, comprising a polymer having a UV screen within it, for example an amphiphilic polymer as defined above; or integrating said composition into said material.

According to other exemplary embodiments the invention provides a method of photoprotecting an organic or mineral glass comprising the step of:

treating said glass with at least one composition including particles of photonic material, more particularly particles having a polymeric multilayer interference structure, comprising a polymer having a UV screen within it, for example an amphiphilic polymer as defined above; or integrating said composition into said glass.

According to other exemplary embodiments the invention provides a method of photoprotecting a material comprising at least natural fibers and/or artificial fibers and/or synthetic fibers such as textiles or papers, the method comprising the step of:

treating said material with at least one composition including particles of photonic material, more particularly particles having a polymeric multilayer interference structure, comprising a polymer having a UV screen within it, for example an amphiphilic polymer as defined above; or integrating said composition into said material.

By way of example, the compositions and films used in the photoprotection methods of the invention have an SPF index, measured before application to the keratinous materials, of at least 10, more preferably 15, more preferably at least 30, 45, or 60. The SPF (Sun Screen Protection Factor) index is defined in the article "*A new substrate to measure sunscreen protection factors throughout the ultraviolet spectrum*", J Soc Cosmet Chem, 40, 127-133 (May/June 1989).

"Fluorescence" Application
Compositions and Films

In other exemplary embodiments the invention provides a cosmetic composition including particles of photonic material, more particularly particles having a polymeric multilayer interference structure, comprising a polymer having a fluorescent agent within it, for example as defined above. The polymer may, for example, be an amphiphilic polymer.

The term "polymer having a fluorescent agent within it" is used to mean that particles having fluorescent properties and that are distinct from the groups forming said polymer are imprisoned in the structure formed by said polymer. In other words, the particles having fluorescent properties are present in addition to said polymer in the structure formed thereby.

Preparation Method

In other exemplary embodiments the invention provides a method of preparing a cosmetic composition including particles of photonic material, in particular particles having a polymeric multilayer interference structure, comprising a polymer having a fluorescent agent within it, for example as defined above, said method comprising:

a) a step of bringing a swelling agent including a dissolved fluorescent agent into contact with a photonic material, in particular having a polymeric multilayer structure;

b) a step of fragmenting a film of photonic material, in particular a film having said polymeric multilayer structure, into particles of photonic material, in particular into particles having a polymeric multilayer structure with a largest dimension of 100 µm or less and/or with a smallest dimension of 100 nm or more; and c) a step of dispersing the particles of photonic material, in particular particles having a polymeric multilayer interference structure obtained after carrying out steps a) and b), in a cosmetically acceptable medium;

step b) being carried out before or after step a).

Uses of Compositions and Films

In other exemplary embodiments the invention provides a method of lightening human keratinous materials, the method comprising the step consisting in applying a cosmetic composition including particles of Photonic material, more particularly particles having a polymeric multilayer interference structure, comprising a polymer having a fluorescent agent within it, for example as defined above.

According to other exemplary embodiments the invention provides a film for lightening the complexion, for application to human keratinous materials, comprising a photonic material, more particularly a polymeric multilayer interference structure, comprising a polymer having a fluorescent agent within it, for example as defined above.

"Coloring" Application
Compositions and Films

In other exemplary embodiments the invention provides a cosmetic composition including particles of photonic material, more particularly particles having a polymeric multilayer interference structure, producing a visible color.

According to other exemplary embodiments the invention provides a cosmetic composition including particles of photonic material, more particularly particles having a polymeric multilayer interference structure, comprising a polymer having a coloring agent within it, for example as defined above.

The term "polymer having a coloring agent within it" is used to mean that a coloring agent that is distinct from the groups forming said polymer is imprisoned in the structure formed by said polymer. In other words, the coloring agent is present in addition to said polymer in the structure formed thereby.

According to other exemplary embodiments the invention provides a film for makeup, for example to even out the complexion, for application to human keratinous materials, the film including particles of photonic material, more particularly particles having a polymeric multilayer interference structure, producing a visible color.

According to other exemplary embodiments the invention provides a film for makeup, for example to even out the complexion, for application to human keratinous materials, the film including a photonic material structure, in particular a polymeric multilayer interference structure, comprising a polymer having a coloring agent within it.

The particles having a polymeric multilayer interference structure may include an amphiphilic polymer as defined above.

Preparation Methods

In other exemplary embodiments the invention provides a method of preparing a cosmetic composition including particles of photonic material, in particular particles having a polymeric multilayer interference structure, for example comprising an amphiphilic polymer, producing a visible color, said method comprising:

a) a step of bringing a swelling agent into contact with a photonic material, in particular having a polymeric multilayer structure;

b) a step of fragmenting a film of photonic material, in particular a film having a polymeric multilayer structure, into particles of photonic material, in particular into particles having a polymeric multilayer structure with a largest dimension of 100 µm or less and/or with a smallest dimension of 100 nm or more; and c) a step of dispersing said particles obtained after carrying out steps a) and b) in a cosmetically acceptable medium;

step b) being carried out before or after step a).

According to other exemplary embodiments the invention provides a method of preparing a cosmetic composition including particles of photonic material, in particular particles having a polymeric multilayer interference structure, comprising a polymer having a coloring agent within it, for example as defined above, said method comprising:

a) a step of bringing a photonic material, in particular having a polymeric multilayer structure, into contact with a swelling agent comprising a dissolved coloring agent;

b) a step of fragmenting a film of photonic material, in particular a film having a polymeric multilayer structure, into particles of photonic material, in particular into particles having a polymeric multilayer structure with a largest dimension of 100 µm or less and/or with a smallest dimension of 100 nm or more; and c) a step of dispersing said particles obtained after carrying out steps a) and b) in a cosmetically acceptable medium;

step b) being carried out before or after step a).

Uses of Compositions and Films

In other exemplary embodiments the invention provides a method of making up, for example to even out the complexion, the method comprising the step consisting in applying to human keratinous materials a cosmetic composition including particles of photonic material, in particular particles having a polymeric multilayer interference structure, for example comprising an amphiphilic polymer as defined above, producing a visible color, said method possibly further comprising a step of selecting a composition as a function of the color and/or the spectral reflectance of the keratinous materials to be treated.

According to other exemplary embodiments the invention provides a method of making up, for example to even out the complexion, the method comprising the step consisting in applying to human keratinous materials a cosmetic composition including particles of photonic material, more particularly particles having a polymeric multilayer interference structure, comprising a polymer having a coloring agent within it, for example an amphiphilic polymer as defined above, said method possibly further comprising a step of selecting the composition as a function of the color and/or the spectral reflectance of the keratinous materials to be treated.

Photonic Materials and Polymeric Multilayer Interference Structures

The particular structural arrangement of the various portions of the material and the dielectric constants of said portions may result in reflection, in at least one direction, of electromagnetic radiation of a particular frequency directed onto the material. The structural arrangement of the various portions of material and the dielectric constants of said portions may form photonic materials that diffract or reflect light about a particular frequency or frequencies. In particular, the polymeric photonic materials contain at least one polymeric portion that is capable of producing a change in at least one physical, chemical, or dielectric characteristic including the dimension, shape, dielectric constant, refractive index, color, or other parameters by means of an altering stimulus. This change has the result of modifying a wavelength of electromagnetic radiation diffracted by the photonic material. As an example, a change in dimension (i.e. volume change) may be produced by swelling, of one of the portions of the photonic material my means of a solvent type swelling agent. The dimensional change may modify the structural arrangement of the photonic material and as a result the dielectric constant of one of the portions of the material, or it may modify the electromagnetic radiation reflected by the photonic material. As an example, a modification of the optical properties may in particular be due to a periodic type spacing between similar portions. The photonic material may comprise a first portion that is reactive to an altering stimulus producing a change in volume or another dimension and a second portion that is non reactive or that is reactive to another type of stimulation.

Photonic materials or photonic crystals are capable of diffracting and/or reflecting electromagnetic radiation over a wide range of wavelengths including the visible, ultraviolet, infrared, and microwave wavelengths. In some circumstances, they may diffract electromagnetic radiation with a wavelength lying in the range 100 nm to 1600 nm. In other circumstances, photonic materials are capable of exhibiting spectacular wavelength shifts of the order of 600% under the action of an external stimulus.

In a particular embodiment of the invention, the dimension of the electromagnetic radiation of at least one of the portions changes relative to another portion such that one wavelength of diffracted electromagnetic radiation is modified by at least 10 nm, at least 25 nm, at least 50 nm, at least 150 nm, at least 200 nm, or at least 250 nm under the influence of an altering stimulus (i.e. swelling agent).

The photonic materials of the invention may also produce changes in the wavelength of the diffracted electromagnetic radiation of at least 50%, at least 25% or at least 10%. As an example, a photonic material of the invention may diffract electromagnetic radiation of more than 700 nm (infrared, microwave), when in the presence of an altering stimulus, the dimension of the electromagnetic radiation of at least one of the portions may change relative to the other portion such that one wavelength of electromagnetic radiation diffracted by the photonic material is modified by at least 1%, 5%, 10%, 25% or more. The percentage change in said diffracted wavelength may be calculated using the following equation:

$$[(\lambda_i - \lambda_0)/\lambda_0] \times 100$$

in which $\lambda_0$ corresponds to the peak of the diffracted wavelength before contact with, or in the absence of, an altering stimulus, and $\lambda_i$ corresponds to the peak of the wavelength diffracted during contact with the altering stimulus.

Photonic materials in accordance with the invention are described in application US 2009/0086208 and they are prepared using the methods indicated in that document.

Photonic Material Films and Particles, in Particular Having a Polymeric Multilayer Interference Structure In the context of the invention, the terms "photonic materials" and in particular the "polymeric multilayer interference structures" encompass films and particles of photonic materials, in particular having a polymeric multilayer interference structure.

In the context of the invention, particles photonic material, in particular particles having a polymeric multilayer interference structure, may be present within a cosmetic composition.

The weight content, relative to the total composition weight, of the particles of photonic material, in particular particles having a polymeric multilayer interference structure, may be in the range 0.1% to 50%, for example in the range 1% to 20%, for example in the range 5% to 15%.

It is also possible to use photonic material films, in particular films having a polymeric multilayer interference structure, said films possibly being applied to keratinous materials as well as to materials such as those mentioned above.

Said films may be deposited locally on a portion of the external surface of the keratinous materials, for example for protection from solar UV radiation, or to lighten the complexion or for making up, for example to even out the complexion.

Said films may be cut into any format and may, for example, be used to conceal skin imperfections: spots, wrinkles, vitiligo, etc The films of the invention may optionally be adhesive. The films may be adhesive, for example when intended for application to keratinous materials, for example the skin. The films of the invention may be formed in situ on the keratinous materials.

Size and Form of the Polymeric Multilayer Interference Structures

FIG. 1 shows a particle having a polymeric multilayer interference structure according to the invention.

In the absence or in the presence of a swelling agent, the length $L_1$ and the width $L_2$ of the particle may be in the range 1 μm to 100 μm.

The thickness $L_3$ of particle may be in the range 0.1 μm to 50 μm in the absence of a swelling agent, and in the range 0.1 μm to 100 μm in the presence of a swelling agent.

In the absence or in the presence of a swelling agent, the particles having a polymeric multilayer interference structure may have a largest dimension of 100 μm or less.

In the absence of a swelling agent, the particles may have a largest dimension of 100 μm or less, for example 75 μm or less, for example 50 μm or less.

In the absence or in the presence of a swelling agent, the particles having a polymeric multilayer interference structure may have a smallest dimension of 0.1 μm or more, for example 1 μm or more.

The film having a polymeric multilayer interference structure may have a largest dimension in the range 1 mm to 50 cm.

The polymeric multilayer interference structures may have a form factor in the range 1 to 1000.

The term "form factor" means the ratio of the largest dimension of the polymeric multilayer interference structure to its smallest dimension.

The polymeric multilayer interference structures may be plate-like, i.e. have a form factor at least equal to 3, for example at least equal to 10.

The polymeric multilayer interference structures may have a lamellar structure, linked to the presence of an amphiphilic polymer, for example. The amphiphilic polymer may have a lamellar structure.

The polymeric multilayer interference structures may comprise at least three layers, for example at least 5, or 50.

The polymeric multilayer interference structures may comprise fewer than 100 layers.

Method for Preparing the Polymeric Multilayer Interference Structure

As mentioned above, the particles having a polymeric multilayer interference structure may be obtained from a photonic gel, which may be produced as described in the publications by E. Thomas: Nat Mat Vol 6, 957-960, 2008 and J Am Chem Soc 2009, 131, 7538-7539.

Figure 2:
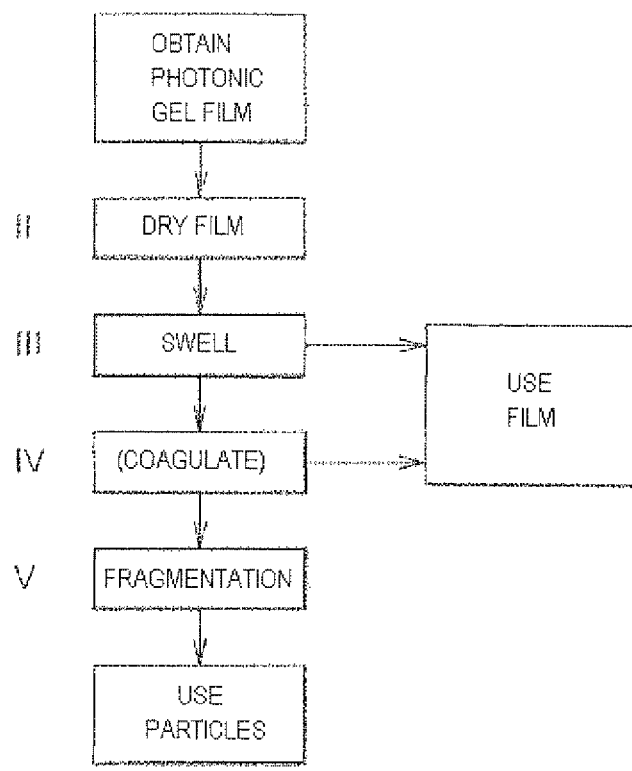

FIG. 2 shows an example of a method of fabricating films and particles having a polymeric multilayer interference structure of the invention.

A photonic gel is obtained in the form of a film (step I), for example by spreading with a film puller, by dip-coating or by spin-coating and by any printing method, for example by ink jet printing a solution of amphiphilic block polymer in a solvent. When deposited on a support, it organizes itself spontaneously into a multilayer polymeric structure, for example a lamellar structure. The photonic gel then comprises alternating hydrophilic and hydrophobic layers.

The number of layers of the multilayer structure of the photonic gel may be 100 or less and its thickness after drying may be 15 μm or less.

After deposition and in the absence of a swelling agent, the photonic gel need not have an interference property in the wavelength range 250 nm to 800 nm.

The photonic gel may be quaternized, for example by contact with 1-bromoethane, as described in the publication Nat Nat Vol 6, 957-960, 2008.

Contact with a swelling agent (step III), of nature that is given in detail below, may cause the photonic gel to swell, for example in its hydrophilic or hydrophobic layers, and thus produce a polymeric multilayer interference structure.

As is detailed below, the step of contact with the swelling agent may be used advantageously in order to introduce one or more UV screens and/or one or more fluorescent agents and/or one or more coloring agents into the polymeric multilayer structure.

The interference wavelength may vary as a function of the concentration, the difference in refractive index between the various layers, the pH of the swelling agent, the molecular weight and the degree of cross-linking the polymers present in the polymeric multilayer interference structure. By varying these parameters, it is possible, for example, to cover the whole WA or UVB spectrum.

In FIGS. 3 and 4, for the purposes of clarity, the relative proportions of the various elements shown have not necessarily been maintained.

FIG. 3 diagrammatically and partially shows a photonic gel 1 deposited on a support S before contact with a swelling agent.

This photonic gel 1 comprises a polymeric multilayer structure that may, for example and as illustrated, be constituted by alternating hydrophilic 10 and hydrophobic 20 lamellar layers.

In the embodiment shown in FIG. 3, the photonic gel is transparent to radiation R having, for example, a wavelength in the range 250 nm to 800 nm.

The term "transparent" means that the photonic gel has no band gap in the wavelength range 450 nm to 800 nm. As an example, the photonic gel may have a transmission factor of 80% or more, for example 90% in the wavelength range under consideration.

FIG. 4 shows the photonic gel 1 of FIG. 3 after contact with a swelling agent. In the example of FIG. 4, only the hydrophobic layers 20 are sensitive to the swelling agent.

In a variation, it is possible for only the hydrophilic layers 10 to be sensitive to the swelling agent.

As shown, contact with a swelling agent may allow a photonic gel 1 to reflect the radiation R and, for example, provide photoprotective properties as regards solar UV radiation and/or produce a visible color. The films of the invention may be used once the swelling step has been carried out.

A coagulation step (step IV) of coagulating the photonic gel may be carried out after bringing the polymeric multilayer structure into contact with the swelling agent, preferably before or after the fragmentation step. It may comprise bringing the polymeric multilayer structure into contact with a coagulation agent that may be an inorganic material such as silica or its precursors, for example TEOS, or a glycol, for example glycerol, dipropylene glycol, sorbitol, butylene glycol, PEGs having molecular weights in the range 400 g/mol to 50000 g/mol. A coagulation step employing a silica precursor, TEOS, in a sol-gel method is described in the publication J Am Chem Soc 2009, 131, 7538-7539.

Carrying out a coagulation step may mean that the particles can retain their physicochemical properties, especially their interference properties, after dispersing them in a cosmetically acceptable medium.

The compositions including particles having a polymeric multilayer interference structure comprising a coagulation agent may retain their interference properties during application and for at least 2 hours, for example 3 hours after applying the composition to the keratinous materials.

The films having a polymeric multilayer interference structure comprising a coagulation agent may retain their interference properties during application and for at least 2 hours, for example 3 hours after applying the composition to the keratinous materials.

Fragmentation step (V) for fragmenting the polymeric multilayer structure of the photonic gel may be carried out, as illustrated in FIG. 2, after the step of making contact with a swelling agent and after any step of making contact with a coagulation agent. In a variation, it is possible to carry out the fragmentation step before the step of making contact with a swelling agent, and then to carry out any coagulation step.

Fragmentation may, for example, be carried out by laser cutting or milling with an air jet, cryomilling, ball milling, or wet milling.

Swelling Agent

In some exemplary embodiments, the photonic material, in particular the polymeric multilayer interference structure, may further include a swelling agent (in particular a non-volatile swelling agent) in a quantity that can swell one or both portions of said material. The swelling agent may, for example, be a mineral oil when the photonic material comprises a polybutadiene/styrene block copolymer in order to swell the polybutadiene portion.

Any appropriate solvent may be used as the swelling agent, such as aqueous or organic solvents, for example. In some particular embodiments of the invention, an acidic, neutral, or basic solvent may be used.

In the context of the invention, the particles of photonic material, in particular particles having a polymeric multilayer interference structure, may include a swelling agent.

The swelling agent may be hydrophilic or hydrophobic depending on the nature of the photonic material portions, in particular the layers of the polymeric multilayer interference structure, which are caused to swell.

The swelling agent may include at least one dissolved optically active material, for example a UV screen, a fluorescent agent, a coloring agent and mixtures thereof.

The optically active material may, for example, be hydrophobic or hydrophilic.

The swelling agent may, for example, comprise a mixture of optically active materials, for example a mixture of a UV screen and a fluorescent agent, a mixture of a UV screen and a coloring agent, a mixture of a fluorescent agent and a coloring agent or indeed a mixture of a UV screen, a fluorescent agent and a coloring agent.

It is possible to use water as the swelling agent, as well as organic or inorganic saline solutions with a concentration in the range 0.01 M to 5 M, for example solutions of sodium, magnesium, potassium, calcium or copper salts, solutions of phosphates, or ammonium salt solutions.

It is also possible to use as the swelling agent, either alone, as a mixture, or in aqueous solution and in any proportions, glycerol, PEGs having a molecular weight in the range 400 g/mol to 50000 g/mol, mono-, di- and oligo-saccharides that are soluble in water in a proportion of at least 1% by weight, sorbitol, propylene glycol, dipropylene glycol, ethylene glycol, butylene glycol, water-soluble polyols, lower alcohols that are miscible in water, for example methanol, ethanol or isopropanol, or 1-butanol.

The term "lower alcohol" means an alcohol having fewer than 6 carbon atoms.

Examples of other suitable solvents that may be mentioned are benzene, acetone, β-methylbutyric acid, α-ethylbutyric acid, 2,2,2,-trifluoroethanol, 1-butanol, 1,4-butanediol, chloroform, bromoethane, methyl acetate, ethyl acetate, dimethylformamide, butan-2-one, divinylbenzene, propylene glycol monomethylether acetate (PGMEA), and acetic acid solutions.

The swelling agent may further comprise or even consist of a UV screen solution, for example organic, neutralized or not neutralized. The following solutions may be mentioned: TEREPHTHALYLIDENE DICAMPHOR SULFONIC ACID, for example Mexoryl SX or PHENYLEENZIMIDAZOLE SULFONIC ACID, for example Eusolex 232.

Using a solution of non-neutralized organic UV screen(s) would mean that the pH could be varied and thus the swelling of the photonic material, especially the polymeric multilayer structure, for example the amphiphilic polymer, can also be varied.

The swelling agent may also be selected from polar oils such as lauroyl isopropyl sarcosinate, octyldodecanol, a $C_{12}$-$C_{15}$ alkylbenzoate (Finsolv TN), undecane and tridecane, for example, as well as oily solutions of organic screens, for example when the particles of photonic material, in particular particles having a polymeric multilayer interference structure, for example the amphiphilic polymer, comprise at least a portion, in particular a layer, which is hydrophobic and sensitive to the swelling agent.

The pH of the swelling agent may be in the range 1 to 12. It may be modified by contact with acids and bases selected, for example, from acetic, lactic, hydrochloric, nitric, sulfuric, maleic, and succinic acid, and bases such as sodium hydroxide, potassium hydroxide, triethanolamine, or solutions of lysine and arginine.

Fixing Agent

The particles of photonic material, in particular particles having a polymeric multilayer interference structure, may include a fixing agent.

A fixing agent may be selected from inorganic compounds, for example silica and its precursors, for example TEOS, or glycols, for example glycerol, dipropylene glycol, sorbitol, butylene glycol, or PEGs having molecular weights in the range 400 g/mol to 50000 g/mol.

The difference in the refractive index of the fixing agent and the layers of the polymeric multilayer interference structure may be in the range 0.05 to 1.5.

Polymers of Photonic Materials and of Polymeric Multilayer Interference Structures The photonic materials, in particular the polymeric multilayer interference structures, of the invention may include homopolymers, copolymers, block copolymers, mixtures of homopolymers, mixtures of block copolymers, mixtures of homopolymers and block copolymers, polymeric materials associated with additives such as colorants, or inorganic compounds.

In some exemplary embodiments, the photonic materials may comprise mixtures of polymers or mixtures of polymers and non-polymers or others, and may include at least two portions with different compositions and/or having different chemical, physical, or dielectric properties.

Furthermore, the photonic materials of the invention may contain other polymeric or non-polymeric additives that may be used to modify the dimension, the chemical or the physical properties of at least one of the portions. In addition, a non-polymeric additive present in the structure of the photonic material may constitute a region separating two portions within the periodic structure. As an example, the size of the separated polymeric portions may be controlled by modifying a fraction of the volume of the portion, for example by incorporating auxiliary nanoparticles, auxiliary homopolymers, auxiliary monomers, or cross-linkable compounds that are polymerized, grafted, and/or cross-linked in situ. The additives such as those mentioned above may be used to modify the number/type of the portion and/or the dimensions of the portion but will not influence the behavior of the photonic material under the influence of an altering stimulus.

Block Copolymer

The block copolymers present in the photonic materials of the invention may result in one-, two- or three-dimensional periodic structures arranged in separate portions characterized by different compositions and/or different physical properties.

The term "periodic structure" is used to mean a structure arranged such that a straight line in at least one direction passes through said structure and intersects at least two separate portions at regular intervals. As an example, a "one-dimensional structure" is a structure that may be oriented in an orthogonal system of coordinates in three dimensions (components in the X, Y, Z directions) such that a straight line in a single direction passes through said structure and intersects at least two separated portions at regular integrals. A "two-dimensional structure" is a structure that may be oriented in a 3-dimensional coordinate system such that straight lines in two directions pass through said structure and intersect at least two separate portions at regular intervals. A "three-dimensional structure" is a structure that may be oriented in a 3-dimensional coordinate system such that a straight line in any of the three directions passes through said structure and intersects at least two separate portions at regular intervals. In addition, the term "periodic structure" refers to a material with portions having a regular periodicity characterized by similar portions having similar dimensions and spacings in the photonic material. The term "portion" defines a distinct region of the photonic material characterized by a particular composition and/or particular physical properties that distinguish it from those of adjacent or surrounding portions.

The polymer constituting the photonic material, in particular the polymeric multilayer interference structure, may be amphiphilic and may comprise or, for example, may be a block copolymer, for example a:
    diblock copolymer with the form A-B where A is a hydrophobic block selected, for example, from: polystyrene, polymethyl methacrylate, polycyclohexyl methacrylate, polyisobornyl acrylate, polyisobornyl methacrylate, polyisobutyl methacrylate, polyethyl methacrylate, poly N-tert butyl acrylamide, and polyisopropyl methacrylate, and B is a:
    hydrophilic and cationic block, for example selected from: poly(2-vinyl pyridine), poly(4-vinyl pyridine), poly(dimethyl amino ethyl methacrylate), poly(diethyl amino ethyl methacrylate), poly(dimethyl amino propyl methacrylamide), and poly(N-vinyl pyrrolidone);
    hydrophilic and anionic block, for example selected from: poly(acrylic acid), poly(methacrylic acid), poly(maleic acid), poly(itaconic acid), poly(fumaric acid), poly(crotonic acid), poly(acrylamido glycolic acid), and poly(acrylamido 2-methylpropane sulfonic acid); or
    hydrophilic and non-ionic block, for example selected from: poly(PEG methacrylate);
    triblock copolymer with the form A-B-C where:
    A and C are different hydrophobic blocks, for example selected from: polystyrene, polymethyl methacrylate, polycyclohexyl methacrylate, polyisobornyl acrylate, polyisobornyl methacrylate, polyisobutyl methacrylate, polyethyl methacrylate, poly N-tert butyl acrylamide, and polyisopropyl methacrylate, and B is a:
    hydrophilic and cationic block, for example selected from: poly(2-vinyl pyridine), poly(4-vinyl pyridine), poly(dimethyl amino ethyl methacrylate), poly(diethyl amino ethyl methacrylate), poly(dimethyl amino propyl methacrylamide), and poly(N-vinyl pyrrolidone);
    hydrophilic and anionic block, for example selected from: poly(acrylic acid), poly(methacrylic acid), poly(maleic acid), poly(itaconic acid), poly(fumaric acid), poly(crotonic acid), poly(acrylamido glycolic acid), and poly(acrylamido 2-methylpropane sulfonic acid); or
    hydrophilic and non-ionic block, for example selected from: poly(PEG methacrylate); or
    B is a hydrophobic block, for example selected from: polystyrene, polymethyl methacrylate, polycyclohexyl methacrylate, polyisobornyl acrylate, polyisobornyl methacrylate, polyisobutyl methacrylate, polyethyl methacrylate, poly N-tert butyl acrylamide, and polyisopropyl methacrylate and A and C are different and selected from:
    hydrophilic and cationic blocks, for example selected from: poly(2-vinyl pyridine), poly(4-vinyl pyridine), poly(dimethyl amino ethyl methacrylate), poly(diethyl amino ethyl methacrylate), poly(dimethyl amino propyl methacrylamide), and poly(N-vinyl pyrrolidone);
    hydrophilic and anionic blocks, for example selected from: poly(acrylic acid), poly(methacrylic acid), poly(maleic acid), poly(itaconic acid), poly(fumaric acid), poly(crotonic acid), poly(acrylamido glycolic acid), and poly(acrylamido 2-methylpropane sulfonic acid); or
    hydrophilic and non-ionic blocks, for example selected from: poly(PEG methacrylate).

The copolymers comprising a hydrophobic block and a hydrophilic and cationic block may be in the salt or quaternized form.

The molecular mass of each of said blocks may be in the range 10000 g/mol to 500000 g/mol.

The copolymers comprising a hydrophobic block and a hydrophilic and anionic block may be in the salt form.

The molecular mass of each of said blocks may vary from 1000 g/mol to 500000 g/mol.

The MPEG may have a molecular weight in the range 500 g/mol to 10000 g/mol.

Whatever the embodiment under consideration, the hydrophilic blocks may be sensitive to the swelling agent.

In a variation, the hydrophobic blocks may be sensitive to the swelling agent. For example, when the hydrophobic block is selected from polyisobornyl acrylate, polyisobornyl methacrylate and polyisobutyl methacrylate, the swelling agent may be a polar oil or a solution of sunscreens dissolved in a polar oil.

The photonic materials, in particular the polymeric multilayer interference structures, may include an amphiphilic polymer, for example having a fluorescent agent within it and/or a UV screen and/or a coloring agent that may be a copolymer.

Particularly preferably, the polymer comprises a polystyrene/poly(2-vinylpyridine)diblock copolymer.

UV Screens

The photonic materials, in particular the polymeric multilayer interference structures, may include a polymer having a UV screen within it, for example an amphiphilic polymer.

The photonic materials, in particular the polymeric multilayer interference structures, and the UV screen present within it may have a complementary screening action for radiation in the wavelength 250 nm to 400 nm.

The choice of UV screen may, for example, be made so that UVA is screened and skin browning is limited.

The UV screens may be organic.

The UV screens may be hydrophobic or hydrosoluble.

The UV screens may be introduced into the photonic material, in particular into the polymeric multilayer interference structure, by means of the swelling agent in which they are dissolved.

UV screens may also be present in the compositions of the invention, in the free state, i.e. outside the photonic materials, in particular outside the polymeric multilayer interference structures.

For the purposes of simplification, a single list of UV screens that can be used as UV screens in the free state or within the photonic materials, in particular the polymeric multilayer interference structures, is given below.

Hydrophobic Screens Capable of Absorbing UV in the Range 320 nm to 400 nm (UVA)

Dibenzoylmethane Derivatives
  Butyl methoxydibenzoylmethane sold in particular under the trade name "PARSOL 1789" by DSM Nutritional Products, Inc;
  isopropyl dibenzoylmethane.

Aminobenzophenones
  n-hexyl 2-(4-diethylamino-2-hydroxybenzoyl)-benzoate sold under the trade name "UVINUL A+" by BASF.

Anthranilic Derivatives
  Menthyl anthranilate sold under the trade name "NEO HELIOPAN MA" by SYMRISE.

4,4-diarylbutadiene derivatives 1,1-dicarboxy(2,2'-dimethyl-propyl)-4,4-diphenylbutadiene.

Hydrophobic Screens Capable of Absorbing UV in the Range 280 nm to 320 nm (UVB)

Para-Aminobenzoates
  Ethyl PABA; "PABA" denotes p-aminobenzoic acid;
  Ethyl dihydroxypropyl PABA;
  Ethylhexyl dimethyl PABA (ESCALOL 507 from ISP).

Salicylic Derivatives
  Homosalate sold under the name "Eusolex HMS" by Rona/EM Industries;
  Ethylhexyl salicylate sold under the name "NEO HELIOPAN OS" by SYMRISE;
  Dipropylene glycol salicylate sold under the name "DIPSAL" by SCHER;
  TEA salicylate, sold under the name "NEO HELIOPAN TS" by SYMRISE.

Cinnamates
  Ethylhexyl methoxycinnamate sold in particular under the trade name "PARSOL MCX" by DSM Nutritional Products, Inc;
  Isopropyl methoxy cinnamate;
  Isoamyl methoxy cinnamate sold under the trade name "NEO HELIOPAN E 1000" by SYMRISE;
  Diisopropyl methylcinnamate;
  Cinoxate;
  Glyceryl ethylhexanoate dimethoxycinnamate.

β,β'-Diphenylacrylate Derivatives
  Octocrylene, sold in particular under the trade name "UVINUL N539" by BASF;
  Etocrylene, sold in particular under the trade name "UVINUL N35" by BASF Benzylidene Camphor Derivatives
  3-Benzylidene camphor manufactured under the trade name "MEXORYL SD" by CHIMEX;
  Methylbenzylidene camphor sold under the trade name "EUSOLEX 6300" by MERCK;
  Polyacrylamidomethyl benzylidene camphor manufactured under the name "MEXORYL SW" by CHIMEX.

Triazine Derivatives
  Ethylhexyl triazone sold in particular under the trade name "UVINUL T150" by BASF;
  Diethylhexyl butamido triazone sold under the trade name "UVASORB HEB" by SIGMA 3V;
  2,4,6-tris(dineopentyl 4'-amino benzalmalonate)-s-triazine;
  2,4,6-tris-(diisobutyl 4'-amino benzalmalonate)-s-triazine;
  2,4-bis(dineopentyl 4'-amino benzalmalonate)-6-(4'-n-butyl aminobenzoate)-s-triazine;
  2,4-bis(n-butyl 4'-amino benzoate)-6-(aminopropyltrisiloxane)-s-triazine;
  symmetrical triazine screens described in patent U.S. Pat. No. 6,225,467, application WO 2004/085412 (see compounds 6 to 9) or the document "Symmetrical Triazine Derivatives", IP.COM Journal, IP.COM INC WEST HENRIETTA, N.Y., US (20 Sep. 2004), in particular 2,4,6-tris-(biphenyl)-1,3,5-triazine (in particular 2,4,6-tris(biphenyl-4-yl-1,3,5-triazine) and 2,4,6-tris(terphenyl)-1,3,5-triazine that is discussed in applications by BEIERSDORF, numbers WO 06/035000, WO 06/034982, WO 06/034991, WO 06/035007, WO 2006/034992, WO 2006/034985.

Imidazoline Derivatives
  Ethylhexyl dimethoxybenzylidene dioxoimidazoline propionate.

Benzalmalonate Derivatives
  Polyorganosiloxanes having a benzalmalonate function, such as polysilicone-15 sold under the trade name "PARSOL SLX" by DSM Nutritional Products, Inc;
  di-neopentyl 4'-methoxybenzalmalonate.

Merocyanin Derivatives
  Octyl-5-N,N-diethylamino-2-phenysulfonyl-2,4-pentadienoate.

Mixed Hydrophobic Screens Capable of Absorbing Both UVA and UVB

Benzophenone Derivatives
  Benzophenone-1 sold under the trade name "UVINUL 400" by BASF;
  benzophenone-2 sold under the trade name "UVINUL D50" by BASF;
  Benzophenone-3 or oxybenzone, sold under the trade name "UVINUL M40" by BASF;
  benzophenone-5;
  benzophenone-6 sold under the trade name "Helisorb 11" by Norquay;
  benzophenone-8 sold under the trade name "Spectra-Sorb UV-24" by American Cyanamid;
  benzophenone-10;
  benzophenone-11;
  benzophenone-12.

Phenyl Benzotriazole Derivatives
  Drometrizole trisiloxane sold under the name "Silatrizole" by RHODIA CHIMIE;
  methylene bis-benzotriazolyl tetramethylbutylphenol, sold in the solid form under the trade name "MIXXIM BB/100" by FAIRMOUNT CHEMICAL or in micronized form in aqueous dispersion under the trade name "TINOSORB M" by CIBA SPECIALTY CHEMICALS.

Bis-Resorcinyl Triazine Derivatives

Bis-ethylhexyloxyphenol methoxyphenyl triazine sold under the trade name "TINOSORB S" by CIBA GEIGY.

Benzoxazole Derivatives 2,4-bis-[5-1(dimethylpropyl)benzoxazol-2-yl-(4-phenyl)-imino]-6-(2-ethylhexyl)-imino-1,3,5-triazine sold under the name Uvasorb $K_2A$ by Sigma 3V.

Hydrosoluble Screens Capable of Absorbing UV in the Range 320 nm to 400 nm (UVA)

Terephthalylidene dicamphor acid sulfonic acid manufactured under the name "MEXORYL SX" by CHIMEX.

Bis-benzoazolyl derivatives as described in patents EP 0 669 323 and U.S. Pat. No. 2,463,264, more particularly the compound disodium phenyl dibenzimidazole tetrasulfonate sold under the trade name "NEO HELIOPAN AP" by Haarmann and REIMER.

Hydrosoluble Screens Capable of Absorbing UV in the Range 280 nm to 320 nm (UVB)

p-Aminobenzoic Derivatives (PABA)
  PABA;
  glyceryl PABA; and
  PEG-25 PABA sold under the name "UVINUL P25" by BASF;
  phenylbenzimidazole sulfonic acid sold in particular under the trade name "EUSOLEX 232" by MERCK;
  ferulic acid;
  salicylic acid;
  DEA methoxycinnamate;
  benzylidene camphor sulfonic acid manufactured under the name "MEXORYL SL" by CHIMEX;
  camphor benzalkonium methosulfate manufactured under the name "MEXORYL SO" by CHIMEX.

Mixed UVA and UVB Hydrosoluble Screens

Benzophenone Derivatives Comprising at Least One Sulfonic Radical

Benzophenone-4 sold under the trade name "UVINUL MS40" by BASF;
  benzophenone-5; and
  benzophenone-9.

Fluorescent Agents

The fluorescent agents possibly present within the photonic materials, in particular the polymeric multilayer interference structures, may be IR or UV fluorescent agents.

The choice of fluorescent agent may, for example, be made so as to screen UVA and limit browning of the skin.

The photonic materials, in particular the polymeric multilayer interference structures, of the invention may include three different types of fluorescent agent respectively producing red, green and blue when illuminated with white light. Such structures can produce white light by additive synthesis and be used in methods of lightening keratinous materials.

The fluorescent agents may be optical brighteners, for example selected from solutions of stilbene derivatives, in particular polystyrylstilbenes and triazinstilbenes, coumarin derivatives, in particular hydroxycoumarins and aminocoumarins, oxazole, benzoxazole, imidazole, triazole or pyrazoline derivatives, pyrene derivatives and porphyrin derivatives, and/or mixtures thereof.

Such compounds are, for example, available under the trade names Tinopal SOP and Uvitex OB from the supplier CIBA GEIGY.

It is also possible to use, as the optical brighteners, aqueous solutions of disodium distyrylbiphenyl disulfonate, for example available under the trade name Tinopal CBS X from the supplier CIBA.

Coloring Agent

The coloring agents may be hydrosoluble liposoluble.

Regardless of the embodiments under consideration, coloring agents may also be present within the photonic materials, in particular within the polymeric multilayer interference structures, or in the free state, i.e. externally of said structures.

As an example, when color applications are desired, the cosmetic composition may include a coloring agent in the free state that may, for example, have substantially the same color as that produced by the particles of photonic material, in particular particles having a polymeric multilayer interference structure. In a variation, the coloring agent in the free state may have a color different from that produced by the particles of photonic material, in particular particles having a polymeric multilayer interference structure.

For the purposes of simplification, a single list of coloring agents for use in the free state or within the photonic materials, in particular the polymeric multilayer interference structures, is given below.

The liposoluble coloring agents may, for example, be selected from: DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, roucou, and curcumin.

The hydrosoluble coloring agents may, for example, be selected from FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanin (beetroot), carmine, chlorophyllin copper, methylene blue, anthocyanins (enocianin, black carrot, hibiscus, elder), and riboflavin.

The coloring agents may also be selected from antraquinones, caramel, carbon black, azulene blues, methoxalene, trioxalene, guaiazulene, chamazulene, rose bengal, cosine 10B, cyanosine, daphinin, juglone, and lawsone.

Optical Properties of Photonic Materials and in Particular of Polymeric Multilayer Interference Structures In the context of the invention, the reflection spectra and transmission factors of the particles of photonic material, in particular the particles having a polymeric multilayer interference structure, are measured before dispersing said particles in a suitable medium.

The reflection and transmission spectra of the photonic material films, in particular of the films having a polymeric multilayer interference structure, are measured before application to the material of interest, in particular to keratinous materials.

The photonic materials, in particular the polymeric multilayer interference structures, of the invention may optionally be goniochromatic.

When the photonic materials, in particular the polymeric multilayer interference structures, produce a visible color, they may optionally have UV screening properties.

When the photonic materials, in particular the Polymeric multilayer interference structures, have UV screening properties, they may optionally produce a visible color.

Application to Photoprotection Against Solar UV Radiation

The photonic materials, in particular the polymeric multilayer interference structures, may, for example, have a reflection spectrum comprising at least one reflection peak in the wavelength range 250 nm to 400 nm, for example in the range 290 nm to 400 nm, for example in the range 330 nm to 400 nm. The reflection peak may be a peak with an order of interference equal to 1.

The photonic materials, in particular the polymeric multilayer interference structures, may, for example, have a reflection spectrum comprising several reflection peaks each corresponding to different orders of interference in the wavelength range 250 nm to 800 nm. Such a reflection spectrum is given, for a photonic gel, in the publication Nat Mat, Vol 6, 957-960, 2008. In such circumstances, the reflection peak in the wavelength range 250 nm to 400 nm may correspond to an order of interference at least equal to 2, for example equal to 3, for example equal to 4, for example equal to 5.

The photonic materials, in particular the polymeric multilayer interference structures, may be transparent in the wavelength range 450 nm to 800 nm.

In the context of the invention, the photonic material, in particular the polymeric multilayer interference structure, is transparent if it has a transmission factor greater than or equal to 80%, for example 90% in the wavelength range under consideration.

The photonic materials, in particular the polymeric multilayer interference structures, may include another optically active material such as a UV screen or a fluorescent agent, for example within the amphiphilic polymer.

The photonic materials, in particular the polymeric multilayer interference structures, and the UV screen, where appropriate, present within them may have a complementary screening action for radiation in the wavelength range 250 nm to 400 nm.

Thus, the cosmetic composition including particles of photonic material, in particular particles having a polymeric multilayer interference structure, comprising a polymer including a UV screen within it, before application to keratinous materials, may have a transmission spectrum comprising at least two minima in the wavelength range 250 nm to 400 nm. The minima may, for example, be separated by at least 50 nm.

Application to Lightening the Complexion

The photonic materials, in particular the polymeric multilayer interference structures, comprising a polymer having a fluorescent agent within it, for example an amphiphilic polymer may have a reflection spectrum comprising a reflection peak in the wavelength range 250 nm to 800 nm, for example 250 nm to 400 nm.

Furthermore, when the photonic materials, in particular the polymeric multilayer interference structures, comprise a polymer including a fluorescent agent within it, before application to the keratinous materials, they may have a transmission spectrum comprising at least two minima in the wavelength range 250 nm to 800 nm.

In these circumstances, a first transmission minimum may be located in the wavelength range 250 nm to 400 nm and a second transmission minimum may be located in the wavelength range 400 nm to 800 nm, for example in the range 400 nm to 500 nm. The minima may, for example, be separated by at least 50 nm, for example 100 nm.

Thus, the cosmetic composition including particles of photonic material, in particular particles having a polymeric multilayer interference structure, comprising a polymer including a fluorescent agent within it, for example an amphiphilic polymer before application to keratinous materials, may have a transmission spectrum comprising two minima in the wavelength range 250 nm to 800 nm.

The minima may be separated by at least 50 nm, for example 100 nm.

At least one minimum may be located in the wavelength range 250 nm to 400 nm and at least one minimum may be located in the wavelength range 400 nm to 800 nm, for example 400 nm to 550 nm.

Application to Makeup

When the photonic materials, in particular multilayer interference structures, are used for their coloring properties, before application to the keratinous materials, they may have a reflection spectrum including at least one reflection peak in the wavelength range 400 nm to 800 nm. Such a reflection spectrum is given for a photonic gel in the publication Nat Mat, Vol 6, 957-960, 2008.

Photonic materials, in particular the polymeric multilayer interference structures, may produce all of the colors of the visible spectrum, for example yellow, yellow-orange or violet.

Photonic materials, in particular the polymeric multilayer interference structures, may produce a metallic color or appearance.

Thus, the composition including particles of photonic material, in particular particles having a polymeric multilayer interference structure, for example comprising an amphiphilic polymer, producing a visible color, before application to keratinous materials, may have a reflection spectrum comprising a reflection peak in the wavelength range 400 nm to 800 nm.

Furthermore, the cosmetic composition including particles of photonic material, in particular particles having a polymeric multilayer interference structure, comprising a polymer including a coloring agent within it, for example an amphiphilic polymer including a coloring agent within it, before application to keratinous materials, may have a reflection spectrum comprising a reflection peak in the wavelength range 400 nm to 800 nm.

The color produced by the coloring agent may reinforce that produced by the photonic material, in particular by the polymeric multilayer interference structure.

Mixture of Particles of Photonic Material, in Particular Particles Having a Polymeric Multilayer Interference Structure The composition of the invention may include a single type of photonic material particles of the invention, in particular having a polymeric multilayer interference structure, or a mixture of at least two different types of photonic material particles, in particular particles having a polymeric multilayer interference structure, for example having respective different transmission and/or reflection spectra in the wavelength range 250 nm to 400 nm.

The composition may, for example, comprise a mixture of one type of photonic material particles, in particular particles having a polymeric multilayer interference structure where the particles comprise an amphiphilic polymer that defines at least two layers of said structure, and another particle type having a multilayer interference structure.

The composition may, for example, comprise a mixture of one type of photonic material particle, in particular particles having a polymeric multilayer interference structure, comprising a polymer having a first UV screen within it and another type of photonic material particles, in particular particles having a polymeric multilayer interference structure, comprising a polymer having a second UV screen within it that differs from the first.

The composition may, for example, comprise a mixture of one type of photonic material particles, in particular particles having a polymeric multilayer interference structure, comprising a polymer having a fluorescent agent within it and another type of photonic material particles, in particular particles having a polymeric multilayer interference structure, producing a visible color.

The composition may, for example, comprise a mixture of one type of photonic material particles, in particular particles having a polymeric multilayer interference structure, comprising a polymer having a fluorescent agent within it and another type of photonic material particles, in particular particles having a polymeric multilayer interference structure, comprising a polymer having a UV screen within it.

The composition may, for example, comprise a mixture of one type of photonic material particles, in particular particles having a polymeric multilayer interference structure, producing a visible color and another type of photonic material particles, in particular particles having a polymeric multilayer interference structure, comprising a polymer having a UV screen within it.

Medium Containing Particles of Photonic Material, in Particular Particles Having a Polymeric Multilayer Interference Structure The particles of photonic material, in particular particles having a polymeric multilayer interference structure, may be contained in a cosmetically acceptable medium, i.e. a non-toxic medium suitable for application to human keratinous materials, in particular the skin, the mucous membranes, or the hair or the nails.

Said medium is adapted to the nature of the support onto which the composition is to be applied and to the form in which the composition is to be packaged.

The medium may comprise a phase that is liquid at 25° C., containing particles of photonic material, in particular particles having a polymeric multilayer interference structure.

The medium may be selected so as to encourage dispersion of the particles of photonic material, in particular particles having a polymeric multilayer interference structure, in the medium before application thereof, in order to prevent the particles of photonic material, in particular particles having a polymeric multilayer interference structure, from becoming aggregated. As an example, it may be possible to use one or more agents that reduce the surface tension of the medium containing the particles of photonic material, in particular particles having a polymeric multilayer interference structure, to less than 35 mN/M.

The term "aqueous medium" denotes a medium that is liquid at ambient temperature and atmospheric pressure and contains a large fraction of water relative to the total weight of the medium. The quantity of water in the aqueous medium is, for example, 30% by weight or more, preferably 40% or more preferably 50%.

The medium may be monophase or multiphase. The compositions of the invention may include an aqueous phase and a fatty phase.

The medium may be transparent or translucent, and colored or not colored. The medium containing the particles of photonic material, in particular particles having a polymeric multilayer interference structure, may contain no pigment or colorant.

The medium may comprise a volatile solvent.

The term "volatile solvent" means any liquid capable of evaporating in contact with keratinous materials, at ambient temperature and at atmospheric pressure.

The medium may in particular be selected such that the composition contains at least 5%, or even at least 30% of volatile solvent.

The medium may comprise a film-forming polymer improving protection persistence.

Film-Forming Polymer in the present invention, the term "film-forming polymer" means a polymer that, by itself or in the presence of an auxiliary film-forming agent, is capable of forming a macroscopically continuous film that adheres to the keratinous material, preferably a cohesive film, and more preferably a film of cohesion and mechanical properties that are such that said film can be isolated and manipulated in isolation, for example when said film is produced by casting over a non-stick surface such as a Teflon or silicone surface.

The composition may comprise an aqueous phase and the film-forming polymer may be present in said aqueous phase. In these circumstances, it is preferably a polymer in dispersion or an amphiphilic or associative polymer.

The term "polymer in dispersion" means polymers that are insoluble in water, in the form of particles of various sizes. The polymer may optionally be cross-linked. The mean particle size is typically in the range 25 nm to 500 nm, preferably in the range 50 nm to 200 nm. The following polymers in aqueous dispersion may be used: Ultrasol 2075® from Ganz Chemical, Daitosol 5000AD® from Daito Kasei, Avalure UR 450® from Noveon, DYNAMX® from National Starch, Syntran 5760® from Interpolymer, Acusol OP 301® from Rohm&Haas, and Neocryl A 1090® from Avecia.

Other examples of aqueous dispersions of particles of hydrodispersible film-forming polymers are acrylic dispersions sold under the names Neocryl. XK-90®, Neocryl A-1070®, Neocryl A-1090®, Neocryl BT-62®, Neocryl A-1079® and Neocryl A-523® by the supplier AVECIA-NEORESINS, Dow Latex 432® by the supplier DOW CHEMICAL, Daitosol 5000 AD® or Daitosol 5000 SJ® by the supplier DAITO KASEY KOGYO, Syntran 5760® by the supplier Interpolymer, Allianz OPT by the supplier ROHM & HAAS, aqueous dispersions of acrylic or styrene/acrylic polymers sold under the trade name JONCRYL® by the supplier JOHNSON POLYMER, or aqueous dispersions of polyurethane sold under the names Neorez R-981® and Neorez R-974® by the supplier AVECIA-NEORESINS, Avalure UR-405®, Avalure UR-410®, Avalure UR-425®, Avalure UR-450®, Sancure 875®, Sancure 861®, Sancure 878® and Sancure 2060® by the supplier GOODRICH, Impranil 85® by the supplier BAYER, Aquamere H-1511® by the supplier HYDROMER, sulfopolyesters sold under the trade name Eastman AQ® by the supplier Eastman Chemical Products, vinyl dispersions such as Mexomere PAM® from the supplier CHIMEX and mixtures thereof.

The term "amphiphilic or associative polymers" means polymers comprising one or more hydrophilic portions that render them partially soluble in water and one or more hydrophobic portions via which the polymers associate or interact. The following associative polymers may be used: Nuvis FX1100® from Elementis, Aculyn 22®, Aculyn 44®), Aculyn 46® from Rohm&Haas, and Viscophobe DB1000® from AMERCHOL. Diblock copolymers constituted by a hydrophilic block (polyacrylate, polyethylene glycol) and a hydrophobic block (polystyrene, polysiloxane) may also be used.

The composition may comprise an oily phase and the film-forming polymer may be present in said oily phase. The polymer may then be in dispersion or in solution. NAD type polymers or microgels (for example KSGs) may be used, as well as polymers of the PS-PA type or copolymers based on styrene (Kraton, Regalite).

Examples of non-aqueous dispersions of polymer particles in one or more silicone and/or hydrocarbon oils that can be stabilized at their surface by at least one stabilizing agent, in particular a block, graft or random polymer, that may be mentioned are acrylic dispersions in isododecane, such as Mexomere PAP® from the supplier CHIMEX, and dispersions of particles of a graft ethylenic polymer, preferably acrylic, in a liquid fatty phase, the ethylenic polymer advantageously being dispersed in the absence of an additional particle surface stabilizer such as that described in particular in the document WO 04/055081.

Film-forming polymers that may be used in the composition of the present invention that may be mentioned are synthetic polymers of the radical or polycondensation type, polymers of natural origin, and mixtures thereof.

In particular, the radical type film-forming polymers may be polymers or copolymers, which are vinyls, especially acrylic polymers.

Vinyl film-forming polymers may result from polymerizing monomers containing an ethylenically unsaturated bond having at least one acid group and/or esters of said acid monomers and/or amides of said acid monomers, such as unsaturated α,β-ethylenically unsaturated carboxylic acids, for example acrylic acid, methacrylic acid, crotonic acid, maleic acid or itaconic acid.

Polymers of natural origin, optionally modified, may be selected from shellac resin, sandarac gum, dammars, elemis, copals, and cellulose polymers such as nitrocellulose, ethylcellulose or nitrocellulose esters selected, for example, from cellulose acetate, cellulose acetobutyrate, cellulose acetopropionate, and mixtures thereof.

The film-forming polymer may be present in the form of solid particles in aqueous or oily dispersion, generally known as a latex or pseudolatex. The film-forming polymer may comprise one or more stable dispersions of particles of generally spherical polymers of one or more polymers, in a physiologically acceptable liquid fatty phase. These dispersions are generally termed polymer NADs, as opposed to latexes that are aqueous polymer dispersions. These dispersions may in particular be in the form of nanoparticles of polymers in stable dispersion in said fatty phase. The nanoparticle size is preferably in the range 5 nm to 600 nm. The techniques for preparing said dispersions are well known to the skilled person.

The composition may comprise at least one film-forming polymer that is a linear block ethylenic film-forming polymer. Said polymer may comprise at least one first sequence (block) and at least one second sequence having different glass transition temperatures (Tg), said first and second sequences being connected together via an intermediate sequence comprising at least one constitutive monomer of the first sequence and at least one constitutive monomer of the second sequence. As an example, the first and second sequences and the block polymer are incompatible with each other. Such polymers, for example, are described in the documents EP 1 411 069 or WO 04/028488, which are herewith incorporated by reference.

Aqueous Phase

The compositions of the invention may include at least one aqueous phase.

The compositions of the invention may include an aqueous phase that may include particles of photonic material, in particular particles having a polymeric multilayer interference structure.

The water content of the aqueous phase is, for example, greater than or equal to 30% by weight, more preferably 40% by weight, highly preferably 50% by weight.

The aqueous phase may also include a mixture of water and (an) organic solvent(s) miscible with water (miscibility in water greater than 50% by weight at 25° C.) such as lower monoalcohols containing 1 to 5 carbon atoms such as ethanol, isopropanol, glycols containing 2 to 8 carbon atoms such as propylene glycol, ethylene glycol, 1,3-butylene glycol, dipropylene glycol, $C_3$-$C_4$ ketones, and $C_2$-$C_4$ aldehydes.

The aqueous phase may be present in an amount in the range 1% to 99% by weight, in particular in the range 3% to 80% by weight, and more particularly in the range 5% to 60% by weight relative to the total weight of the composition under consideration.

Fatty Phase

In all of the embodiments under consideration, the compositions of the invention may include a fatty phase.

The fatty phase may, for example, be free of particles of photonic material, in particular particles having a polymeric multilayer interference structure.

The composition may comprise an oil such as, for example, synthesized esters or ethers, linear or branched hydrocarbons of mineral or synthetic origin, fatty alcohols containing 8 to 26 carbon atoms, partially fluorinated hydrocarbon and/or silicone oils, silicone oils such as polymethylsiloxanes (PDMS), which may optionally be volatile, with a linear or cyclic silicone chain, which may be liquid or pasty at ambient temperature, and mixtures thereof; other examples are given below.

A composition in accordance with the invention may thus comprise at least one volatile oil.

Volatile Oils

In the context of the present invention, the term "volatile oil" means an oil (or non-aqueous medium) that is capable of evaporating on contact with skin in less than one hour, at ambient temperature and at atmospheric pressure.

The volatile oil is a volatile cosmetic oil, liquid at ambient temperature, in particular having a non-zero vapor pressure, at ambient temperature and atmospheric pressure, in particular having a vapor pressure in the range 0.13 Pa to 40000 Pa ($10^{-3}$ mmHg to 300 mmHg), in particular in the range 1.3 Pa to 13000 Pa (0.01 mmHg to 100 mmHg), and more particularly in the range 1.3 Pa to 1300 Pa (0.01 mmHg to 10 mmHg).

The volatile hydrocarbon oils may be selected from hydrocarbon oils of animal or vegetable origin containing 8 to 16 carbon atoms, and in particular branched $C_8$-$C_{16}$ alkanes (also termed isoparaffins), such as isododecane (also termed 2,2,4,4,6-pentamethylheptane), isodecane, isohexadecane and, for example, oils sold under the trade names Isopars® or Permethyls®.

Examples of volatile oils that may also be used are volatile silicones, for example linear or cyclic volatile silicone oils, especially those with a viscosity of ≤8 centistokes (cSt) ($8×10^{-6}$ m$^2$/s) especially containing 2 to 10 silicon atoms, in particular 2 to 7 silicon atoms, said silicones optionally comprising alkyl or alkoxy groups containing 1 to 10 carbon atoms. Examples of volatile silicone oils that may be used in the invention that may be mentioned are dimethicones with a viscosity of 5 cSt to 6 cSt, octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane, dodecamethyl pentasiloxane, and mixtures thereof.

It is also possible to use fluorinated volatile oils such as nonafluoromethoxybutane or perfluoromethylcyclopentane, and mixtures thereof.

It is also possible to use a mixture of the oils mentioned above.

Non-Volatile Oils

A composition of the invention may comprise a non-volatile oil.

Within the context of the present invention, the term "non-volatile oil" means an oil having a vapor pressure of less than 0.13 Pa, in particular high molecular mass oils.

The non-volatile oils may in particular be selected from hydrocarbon oils, fluorinated if necessary, and/or non-volatile silicone oils.

Examples of non-volatile hydrocarbon oils that may be suitable for implementing the invention that may in particular be mentioned are:

hydrocarbon oils of animal origin;

hydrocarbon oils of vegetable origin, such as phytostearyl esters, for example phytostearyl oleate, phytostearyl isostearate or lauroyl/octyldodecyl/phytostearyl glutamate sold, for example, under the name ELDEW PS203 by AJINOMOTO, triglycerides constituted by esters of fatty acids and glycerol wherein the fatty acids may have chain lengths in the range $C_4$ to $C_{24}$, and may be linear or branched, saturated or unsaturated; said oils are in particular heptanoic or octanoic triglycerides, or wheatgerm, sunflower, grapeseed, sesame, corn, apricot, castor, shea, avocado, olive, soya, sweet almond, palm, rape, cottonseed, hazelnut, macadamia nut, jojoba, alfalfa, poppy, Hokkaido squash, gourd, blackcurrant, evening primrose, millet, barley, quinoa, rye, carthame, bancoulier, passiflora, or musk rose oils; shea butter; or caprylic/capric acid triglycerides such as those sold by the supplier STEARINERIES DUBOIS or those sold under the names MIGLYOL 810®, 812® and 818® by the supplier DYNAMIT NOBEL;

hydrocarbon oils of mineral or synthetic origin such as, for example:

synthesized ethers containing 10 to 40 carbon atoms;

linear or branched hydrocarbons of mineral or synthetic origin, such as vaseline, polydecenes, hydrogenated polyisobutene such as parleam, squalane and mixtures thereof, and in particular hydrogenated polyisobutene;

synthesized esters such as oils with formula $R_1COOR_2$, wherein $R_1$ represents the residue of a linear or branched fatty acid containing 1 to 40 carbon atoms and $R_2$ represents a hydrocarbon chain, especially branched, containing 1 to 40 carbon atoms, provided that $R_1+R_2 \geq 10$.

The esters may be in particular be selected from esters, in particular of fatty acids, such as, for example:

cetostearyl octanoate, esters of isopropyl alcohol such as isopropyl myristate, isopropyl palmitate, ethyl palmitate, 2-ethylhexyl palmitate, isopropyl stearate or isostearate, isostearyl isostearate, octyl stearate, hydroxyl esters such as isostearyl lactate, octyl hydroxystearate, diisopropyl adipate, heptanoates, in particular isostearyl heptanoate, octanoates, decanoates or ricinoleates of alcohols or polyalcohols, such as propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethyl hexanoate and mixtures thereof, $C_{12}$-$C_{15}$ alcohol benzoates, hexyl laurate, neopentanoic acid esters such as isodecyl neopentanoate, isotridecyl neopentanoate, isostearyl neopentanoate, octyldodecyl neopentanoate, isononanoic acid esters such as isononyl isononanoate, isotridecyl isononanoate, octyl isononanoate, or hydroxyl esters such as isostearyl lactate, or di-isostearyl malate;

esters of polyols, and pentaetrythritol esters, such as dipentaerythritol tetrahydroxystearate/tetraisostearate;

esters of diol dimers and diacid dimers, such as Lusplan DD-DA5® and Lusplan DD-DA7®, sold by the supplier NIPPON FINE CHEMICAL and described in application FR 03 02809;

fatty alcohols that are liquid at ambient temperature having a branched and/or unsaturated carbon chain containing 12 to 26 carbon atoms, such as 2-octyldodecanol, isostearyl alcohol, oleic alcohol, 2-hexyldecanol, 2-butyloctanol, or 2-undecylpentadecanol;

higher fatty acids such as oleic acid, linoleic acid, linolenic acid and mixtures thereof; and dialkyl carbonates, the 2 alkyl chains possibly being identical or different, such as dicaprylyl carbonate sold under the name Cetiol CC®, by Cognis;

non-volatile silicone oils such as, for example, non-volatile polydimethylsiloxanes (PDMS), polydimethylsiloxanes comprising pendant alkyl or alkoxy groups and/or with silicone chain ends, the groups each containing 2 to 24 carbon atoms, phenyl silicones such as phenyl trimethicones, phenyl dimethicones, phenyl trimethylsiloxy diphenylsiloxanes, diphenyl dimethicones, diphenyl methyldiphenyl trisiloxanes, or 2-phenylethyl trimethylsiloxysilicates, or dimethicones or phenyltrimethicone with a viscosity less than or equal to 100 cSt, and mixtures thereof;

and mixtures thereof.

Surfactants

The composition of the invention may further contain emulsifying and co-emulsifying surfactants present, for example, in a proportion in the range 0.1% to 30% by weight relative to the total composition weight.

Said surfactants may be selected from anionic or non-ionic surfactants. Reference should be made to the document "The Encyclopedia of Chemical Technology, KIRK-OTHMER, volume 22, pp 333-432, third edition, 1979, WILEY, for a definition of the properties and functions of the surfactants, in particular pp 347-377 of said reference, for the anionic and non-ionic surfactants.

Examples of surfactants that may be employed in the invention and are suitable for producing a W/O emulsion that may be mentioned are dimethicone copolyols such as the mixture of cyclomethicone and dimethicone copolyol sold under the name DC 5225 C by the supplier Dow Corning, and dimethicone copolyols such as laurylmethicone copolyol sold under the name Dow Corning 5200 Formulation Aid by the supplier Dow Corning and cetyl dimethicone copolyol sold under the name ABIL EM 90R by the supplier GOLDSCHMIDT, or the polyglyceryl-4 isostearate/cetyl dimethicone copolyol/hexyllaurate mixture sold under the name ABIL WE 09 by the supplier GOLDSCHMIDT.

It is possible to add thereto one or more co-emulsifying agents that may, for example, be selected from the group comprising alkylated polyol esters. Particular examples of alkylated polyol esters that may be mentioned are esters of glycerol and/or sorbitan, for example polyglycerol isostearate, such as the composition sold under the name Isolan GI 34 by the supplier GOLDSCHMIDT, sorbitan isostearate, such as the composition sold under the name ARLACEL 987 by the supplier ICI, sorbitan and glycerol isostearate, such as the composition sold under the name ARLACEL 986 by the supplier ICI, and mixtures thereof.

Polyisobutylene surfactants containing esterified succinic end groups, such as those sold under the names Lubrizol 5603 and Chemcinnate 2000 by the suppliers Lubrizol and Chemron, may also be used as emulsifiers suitable for obtaining a W/O emulsion.

Surfactants for W/O emulsions that may also be used include a solid cross-linked elastomeric organopolysiloxane comprising at least one oxyalkylene group, such as those obtained according to the procedure of Examples 3, 4 and 8 of document U.S. Pat. No. 5,412,004 and of the examples of document U.S. Pat. No. 5,811,487, especially the product of Example 3 (synthesis example) of patent U.S. Pat. No. 5,412,004, and such as the product sold under the reference KSG 21 by the supplier Shin-Etsu.

Examples of surfactants that may be used in the invention that are suitable for obtaining an O/W emulsion that may be mentioned are non-ionic surfactants, and especially esters of polyols and of fatty acids with a saturated or unsaturated chain containing, for example, 8 to 24 carbon atoms and more preferably 12 to 22 carbon atoms, and their oxyalkylenated derivatives, i.e. derivatives containing oxyethylenated and/or oxypropylenated units, such as the glyceryl esters of $C_8$-$C_{24}$ fatty acids, and their oxyalkylenated derivatives; polyethylene glycol esters of $C_8$-$C_{24}$ fatty acids, and their oxyalkylenated derivatives; sorbitol esters of $C_8$-$C_{24}$ fatty acids, and their oxyalkylenated derivatives; sugar (sucrose, glucose or alkylglucose) esters of $C_8$-$C_{24}$ fatty acids, and their oxyalkylenated derivatives; ethers of fatty alcohols; sugar ethers of $C_8$-$C_{24}$ fatty alcohols; oxyethylenated fatty acid ethers of glucose or alkylglucose; and mixtures thereof.

Glyceryl esters of fatty acids that may in particular be mentioned include glyceryl stearate (glyceryl mono-, di- and/or tristearate) (CTFA name: glyceryl stearate) or glyceryl ricinoleate, and mixtures thereof.

Polyethylene glycol esters of fatty acids that may in particular be mentioned include polyethylene glycol stearate (polyethylene glycol mono-, di- and/or tristearate) and more especially polyethylene glycol 50 OE monostearate (CTFA name: PEG-50 stearate), polyethylene glycol 100 OE monostearate (CTFA name: PEG-100 stearate) and mixtures thereof.

It is also possible to use mixtures of these surfactants, such as the product containing glyceryl stearate and PEG-100 stearate, sold under the name ARLACEL 165 by the supplier Uniqema, and the product containing glyceryl stearate (glyceryl mono-distearate) and potassium stearate, sold under the name TEGIN by the supplier GOLDSCHMIDT (CTFA name: glyceryl stearate SE).

Fatty acid esters of glucose or of alkylglucose that may in particular be mentioned include glucose palmitate, alkylglucose sesquistearates, such as methyl glucose sesquistearate, alkylglucose palmitates, such as methylglucose or ethylglucose palmitate, fatty esters of methylglucoside and more especially the diester of methylglucoside and of oleic acid (CTFA name: Methyl glucose dioleate); the mixed ester of methylglucoside and of the oleic acid/hydroxystearic acid mixture (CTFA name: Methyl glucose dioleate/hydroxystearate); the ester of methylglucoside and isostearic acid (CTFA name: Methyl glucose isostearate); the ester of methylglucoside and lauric acid (CTFA name: Methyl glucose laurate); the mixture of the monoester and diester of methylglucoside and isostearic acid (CTFA name: Methyl glucose sesqui-isostearate); the mixture of the monoester and diester of methylglucoside and stearic acid (CTFA name: Methyl glucose sesquistearate) and in particular the product sold under the name Glucate SS by the supplier AMERCHOL, and mixtures thereof.

Examples of oxyethylenated ethers of a fatty acid and glucose or alkylglucose that may be mentioned include the oxyethylenated ethers of a fatty acid and methylglucose, for example the polyethylene glycol ether of the diester of methyl glucose and stearic acid containing approximately 20 mol of ethylene oxide (CTFA name: PEG-20 methyl glucose distearate), such as the product sold under the name Glucam E-20 distearate by the supplier AMERCHOL; the polyethylene glycol ether of the mixture of the monoester and diester of methylglucose and stearic acid containing about 20 mol of ethylene oxide (CTFA name: PEG-20 methyl glucose sesquistearate), for example the product sold under the name Glucamate SSE-20 by the supplier AMERCHOL, and the product sold under the name Grillocose PSE-20 by the supplier GOLDSCHMIDT, and mixtures thereof.

Examples of sucrose esters that may be mentioned include saccharose palmitostearate, saccharose stearate and saccharose monolaurate. Examples of ethers of fatty alcohols that may be mentioned include polyethylene glycol ethers of fatty alcohols containing 8 to 30 carbon atoms and especially 10 to 22 carbon atoms, such as polyethylene glycol ethers of cetyl alcohol, stearyl alcohol or cetearyl alcohol (mixture of cetyl and stearyl alcohol). Examples that may be mentioned include ethers comprising 1 to 200 and preferably 2 to 100 oxyethylene groups, such as those with CTFA name Ceteareth-20 and Ceteareth-30, and mixtures thereof.

Sugar ethers that may in particular be mentioned are alkylpolyglucosides, for example decylglucoside, such as the product sold under the name MYDOL 10 by the supplier Mao Chemicals, the product sold under the name PLANTAREN 2000 by the supplier Henkel, and the product sold under the name ORAMIX NS10 by the supplier SEPPIC; caprylyl/capryl glucoside, such as the product sold under the name ORAMIX CG 110 by the supplier SEPPIC or under the name LUTENSOL GD 70 by the supplier BASF; laurylglucoside, such as the products sold under the names PLANTAREN 1200 N and PLANTACARE 1200 by the supplier Henkel; cocoglucoside, such as the product sold under the name PLANTACARE 818/UP by the supplier Henkel; cetostearyl glucoside optionally as a mixture with cetostearyl alcohol, sold, for example, under the name MONTANOV 68 by the supplier SEPPIC, under the name TEGO-CARE CG90 by the supplier GOLDSCHMIDT and under the name EMULGADE KE3302 by the supplier Henkel; arachidyl glucoside, for example in the form of the mixture of arachidyl alcohol and behenyl alcohol and arachidyl glucoside, sold under the name MONTANOV 202 by the supplier SEPPIC; cocoylethylglucoside, for example in the form of a mixture (35/65) with cetyl and stearyl alcohol, sold under the name MONTANOV 82 by the supplier SEPPIC, and mixtures thereof.

The composition according to the invention may also contain amphiphilic polymers as emulsifiers or co-emulsifiers.

The term "amphiphilic polymer" means any polymer comprising both a hydrophilic portion and a hydrophobic portion separating two liquids of different polarity and thus allowing liquid-liquid dispersions of a direct, inverse or multiple type to be stabilized.

The amphiphilic polymer may reduce the water/oil interfacial tension to 10 mN/m, irrespective of the oil. These polymers are ionic (anionic or cationic) or amphoteric.

The amphiphilic polymers in accordance with the invention generally have a number average molecular weight in the range 1000 g/mol to 20000000 g/mol, preferably in the range 20000 to 8000000, for example in the range 100000 g/mol to 700000 g/mol. The quantity of amphiphilic polymer used in accordance with the invention may be in the range 0.01% to 20% by weight, preferably 0.1% to 10% by weight, for example 0.2% to 5% by weight.

Particular examples that may be used are acrylate/$C_{10}$-$C_{30}$—alkylacrylate copolymers such as the products sold under the names PEMULEN TR1, PEMULEN TR2 and CARBOPOL 1382 by the supplier GOODRICH, or mixtures thereof. It is also possible to use acrylate/steareth-20 itaconate copolymers and acrylate/ceteth-20 itaconate copolymers sold under the names STRUCTURE 2001 and STRUCTURE 3001 by the supplier NATIONAL STARCH. Particularly suitable cross-linked or non cross-linked amphiphilic polymers are the products sold under the names ARISTOFLEX LNC, ARISTOFLEX SNC, and ARISTOFLEX HMS by the supplier CLARIANT.

An example of a terpolymer that may be mentioned is the methacrylic acid/methyl acrylate/behenyl dimethyl-m-isopropenylbenzylisocyanate terpolymer ethoxylated with 40 EO units, sold by the supplier AMERCHOL under the names VISCOPHOBE DB 1000 NP3-NP4.

It is also possible to mention cross-linked terpolymers of methacrylic acid, ethyl acrylate, Polyethylene glycol stearyl ether (10 EO) (Steareth 10), such as those sold by the supplier ALLIED COLLOIDS under the name SALCARE SC 80.

Examples of anionic polymers for use in the invention are polymers of isophthalic acid or sulfoisophthalic acid, in particular copolymers of phthalate/sulfoisophthalate/glycol (for example diethylene glycol/phthalate/isophthalate/1,4-cyclohexanedimethanol) sold under the name "Eastman AQ Polymer" (AQ 35S, AQ 385, AQ 55S and AQ 48 Ultra) by the supplier Eastman Chemical.

Additives

The composition comprising the particles of photonic material, in particular particles having a polymeric multilayer interference structure, may comprise at least one additive selected from adjuvants that are normal in the cosmetics field, such as fillers, softening agents, coloring agents, surfactants, hydrophilic or lipophilic gelling agents, active ingredients, either hydrosoluble or liposoluble, preservatives, moisturizers such as polyols and in particular glycerin, sequestering agents, antioxidants, solvents, fragrances, physical and chemical sunscreens, especially against UVA and/or UVB, odor absorbers, pH adjusting agents (acids or bases), and mixtures thereof.

The composition may contain at least one active ingredient having a complementary activity in the solar protection field, such as antioxidants, whitening agents in the context of anti-pigmentation and depigmentation, or anti-ageing active ingredients.

The additive or additives may be selected from those cited in the CTFA Cosmetic Ingredient Handbook, 10$^{th}$ Edition, Cosmetic and Fragrance Assn, Inc, Washington D.C. (2004), herewith incorporated by reference.

Galenical Dosage Forms

The particles of photonic material, in particular particles having a polymeric multilayer interference structure, may be used in lotions, creams, milks, balms, pommades, gels, emulsions, films, patches, sticks, for example lipsticks, powders, or pastes, for the skin, the lips, the hair or the nails.

The particles of the invention may, for example, be incorporated into any type of cosmetic composition, for example of the gloss, lipstick, eye-liner, mascara, foundation, eye-shadow, nail polish etc type.

The photonic material films, in particular films having a polymeric multilayer interference structure of the invention, may be applied by transfer. Before application to the keratinous materials, said films may be attached to an adhesive layer.

When the cosmetic composition of the invention is used to protect the hair against solar UV radiation, it may be in the form of a shampoo, lotion, gel, emulsion, or non-ionic vesicular dispersion, and may, for example, constitute a rinse-out composition, a composition for application before or after shampooing, before or after coloring or stripping, before, during or after perming or straightening, as a setting or treatment lotion, a lotion or gel for blow drying or setting, a perming or straightening composition, or for coloring or stripping the hair.

Modes of Application

The composition including particles of photonic material, in particular particles having a polymeric multilayer interference structure, may be applied with the hand or using an applicator.

Application may also be accomplished by spraying or projection using a piezoelectric device, for example, or by transfer of a layer of composition that has been deposited on an intermediate support.

Packaging

The composition may be packaged in any packaging device, especially formed from thermoplastic material, or on any support provided for that purpose.

The packaging device may be a bottle, a pump bottle, an aerosol bottle, a tube, a sachet, or a pot.

EXAMPLES

Example 1

A gel of polystyrene-poly(2-vinylpyridine) quaternised diblock copolymer (PS-b-Q-P2VP) (190K/190K) with a thickness of 3 μm (dry) was obtained by dip coating, on a rigid surface, from a 5% by weight PS-b-Q-P2VP solution in propylene glycol monomethyl ether acetate. The gel was then swollen using an aqueous 2.5 M $NH_4Cl$ solution. A photonic gel interfering in the wavelength range 340 nm to 385 nm was obtained. This photonic gel film was suitable for use as a photoprotective agent for keratinous materials.

Example 2

The gel from Example 1 was detached from the rigid support then fragmented before swelling into particles with a largest dimension of less than 50 μm using a dry ball mill. The particles thus obtained were then dispersed in an aqueous 2.5 M $NH_4Cl$ solution.

After separating by filtration, particles having a polymeric multilayer interference structure interfering in the UV range (between 340 nm and 385 nm) were obtained.

Example 3

A 3 μm thick (dry) PS-b-Q-P2VP (190K/190K) gel was spread over a rigid support then fragmented before swelling into particles with a largest dimension of less than 50 μm using a dry ball mill. The particles thus obtained were then dispersed in a mixture containing 50% by weight of glycerol and 50% by weight of an aqueous 2.5 M $NH_4Cl$ solution. After separating, particles having a polymeric multilayer interference structure interfering in the wavelength range 340 nm to 385 nm were obtained.

Introducing glycerol had the effect of preserving the interference properties of the photonic gel after drying.

Example 4

Photoprotective Cosmetic Composition Based on Photonic Gel Particles

Fatty Phase

| | |
|---|---|
| ARISTOFLEX LNC (CLARIANT) | 1% |
| Cyclopentasiloxane | 6% |
| Octylpalmitate | 6% |

Aqueous Phase

| Particles of photonic gel produced in Example 3 | 10% |
|---|---|
| Glycerol | 5% |
| Preservative | 0.3% |
| Water qsp | 100% |

Example 5

Production of Photonic Gel Particles Coagulated with Silica

A 3 μm thick (dry) PS-b-Q-P2VP (190K/190K) gel was obtained by dip coating, on a rigid surface, from a 5% PS-b-Q-P2VP solution in propylene glycol monomethyl ether acetate. The gel was then fragmented, before swelling into particles with a largest dimension of less than 50 μm using a dry ball mill. The particles obtained were then dispersed and swollen in methanol.

An aqueous solution of TEOS (tetraethoxysilane) with a concentration 0.45 M was then added. An aqueous 2.5 M $NH_4Cl$ solution was added with vigorous stirring. Particles having a polymeric multilayer interference structure interfering in the wavelength range 340 nm to 385 nm and insensitive to the dispersion medium were obtained.

Example 6

Photonic Gel Swollen with an Aqueous Sunscreen Solution

A 3 μm thick (dry) PS-b-Q-P2VP (190K/190K) gel was obtained by dip coating, on a rigid surface, from a 5% PS-b-Q-P2VP solution in propylene glycol monomethyl ether acetate. This gel was then swollen with an aqueous 3% solution of Mexoryl SX (Chimex) (TEREPHTHALYLIDENE DICAMPHOR SULFONIC ACID, 33% in water). A photonic gel interfering in the wavelength range 330 nm to 385 nm with a significantly reduced goniochromatic effect was thus obtained.

Said photonic gel film was suitable for use as a photoprotective agent for keratinous materials.

Example 7

Photonic Gel Swollen with an Aqueous Sunscreen Solution

A 3 μm thick (dry) PS-b-Q-P2VP (190K/190K) gel was obtained by dip coating, on a rigid surface, from a 5% PS-b-Q-P2VP solution in propylene glycol monomethyl ether acetate. This gel was swollen with an aqueous 0.5% solution of Eusolex 232 (Merck) (PHENYLBENZIMIDAZOLE SULFONIC ACID). A photonic gel interfering in the wavelength range 290 nm to 385 nm was thus obtained.

Said photonic gel film was suitable for use as a photoprotective agent for keratinous materials.

Example 8

Photoprotective Cosmetic Composition Comprising Two Types of Particles with Polymeric Multilayer Interference Structures that Interfere Differently and in a Complementary Manner with UV Fatty Phase

| ARISTOFLEX LNC (CLARIANT) | 1% |
|---|---|
| Cyclopentasiloxane | 6% |
| Octylpalmitate | 6% |

Aqueous Phase

| Particles having a polymeric multilayer interference structure obtained by ball milling a photonic gel from Example 6 | 5% |
|---|---|
| Particles having a polymeric multilayer interference structure obtained by ball milling a photonic gel from Example 7 | 5% |
| Glycerol | 5% |
| Preservative | 0.3% |
| Water qsp | 100% |

Example 9

Photoprotective Cosmetic Composition Comprising Two Types of Particles with Polymeric Multilayer Interference Structures that Interfere Differently and in a Complementary Manner with UV Fatty Phase

| ARISTOFLEX LNC (CLARIANT) | 1% |
|---|---|
| Cyclopentasiloxane | 6% |
| Octylpalmitate | 6% |

Aqueous Phase

| Particles having a polymeric multilayer interference structure from Example 2 | 5% |
|---|---|
| Particles having a polymeric multilayer interference structure similar to those of Example 1 but swollen with a 1M solution of $NH_4Cl$ obtained using the method of Example 2 | 5% |
| Glycerol | 5% |
| Preservative | 0.3% |
| Water qsp | 100% |

Example 10

Photonic Gel Swollen with an Optical Brightener Solution

A 3 μm thick (dry) PS-b-Q-P2VP (190K/190K) gel was obtained by dip coating, on a rigid surface, from a 5% PS-b-Q-P2VP solution in propylene glycol monomethyl ether acetate. Said gel was then swollen with an aqueous 0.5% solution of Tinopal CBS X (CIBA) (DISODIUM DISTYRYLBIPHENYL DISULFONATE). A photonic gel interfering in the UV region and colored blue was obtained that was suitable, once fragmented, for use in lightening human keratinous materials, for example the skin.

Example 11

Colored Photonic Gel

A 3 µm thick (dry) PS-b-Q-P2VP (190K/190K) gel was obtained by dip coating, on a rigid surface, from a 5% PS-b-Q-P2VP solution in propylene glycol monomethyl ether acetate. Said gel was then swollen with an aqueous 1.5 M $NH_4Cl$ solution. The reflected wavelength corresponding to the transmission minimum was approximately 550 nm, i.e. a yellow color.

The film was suitable, for example, for use to even out the complexion either before or after fragmentation.

Example 12

Colored Photonic Gel

A 3 µm thick (dry) PS-b-Q-P2VP (190K/190K) gel was obtained by dip coating, on a rigid surface, from a 5% PS-b-Q-P2VP solution in propylene glycol monomethyl ether acetate. Said gel was swollen with an aqueous 0.5 M $NH_4Cl$ solution. The reflected wavelength corresponding to the transmission minimum was approximately 410-420 nm, i.e. a violet color.

The film was suitable, for example, for use to even out the complexion either before or after fragmentation.

Example 13

Colored Photonic Gel

A 3 µm thick (dry) PS-b-Q-P2VP (190K/190K) gel was obtained by dip coating, on a rigid surface, from a 5% PS-b-Q-P2VP solution in propylene glycol monomethyl ether acetate. Said gel was then swollen with an aqueous 1 M $NH_4Cl$ solution. The reflected wavelength corresponding to the transmission minimum was approximately 600 nm, i.e. a yellow-orange color. The film was suitable, for example, for use to even out the complexion either before or after fragmentation.

The photonic gels described in Examples 11 to 13 could be fragmented using the method of Example 2.

The photonic gels described above, for example the colored photonic gels of Examples 11 to 13, could be coagulated by the action of a silica precursor (TEOS) or with glycerol, as in Example 3.

Example 14

Reflection Spectrum of a Photonic Gel

FIG. 5 shows two absorption spectra of a PS-P2VP photonic gel from the publication Nat. Mat. Vol 6, 957-960, 2008.

The absorption peaks measured correspond to the transmission minima and to the reflection peaks of the photonic gel.

In the absence of a swelling agent, the absorption spectrum had no peak and the photonic gel did not have interference properties.

In contrast, when the photonic gel was swollen with pure water, the absorption spectrum could, as shown, have 5 reflection bands each corresponding to a distinct order of interference. The peak in the UV in this example corresponds to an order of interference of 5.

Unless otherwise specified, the expression "comprising a" should be construed as meaning "comprising at least one".

The invention claimed is:

1. A photoprotective cosmetic composition including particles having a polymeric multilayer interference structure, at least two layers of said structure comprising an amphiphilic polymer, wherein the particles include a swelling agent, the swelling agent including at least one optically active material, the at least one optically active material being dissolved in the swelling agent and being included within the amphiphilic polymer, wherein the amphiphilic polymer comprises a diblock copolymer with the form A-B where A is polystyrene and B is poly(2-vinyl pyridine), wherein the blocks of the diblock copolymer have the same number average molecular weight, wherein the diblock copolymer has a periodic structure having two separate blocks of A-B alternated at regular intervals, and wherein each block of the diblock copolymer has a number average molecular weight of from 1,000 g/mol to 500,000 g/mol, and wherein the particles having a polymeric multilayer interference structure include a fixing agent selected from inorganic materials, glycols, and PEGs having a number average molecular weight in a range of from 400 g/mol to 50,000 g/mol.

2. The composition according to claim 1, wherein the particles having a polymeric multilayer interference structure have a reflection spectrum including a reflection peak in a wavelength range of from 250 nm to 400 nm.

3. A photoprotective cosmetic composition including particles having a polymeric multilayer interference structure, at least two layers of said structure comprising an amphiphilic polymer, the photoprotective cosmetic composition comprising a fatty phase and an aqueous phase, the aqueous phase including the particles having a polymeric multilayer interference structure, wherein the amphiphilic polymer comprises a diblock copolymer with the form A-B where A is polystyrene and B is poly(2-vinyl pyridine), wherein the blocks of the diblock copolymer have the same number average molecular weight, wherein the diblock copolymer has a periodic structure having two separate blocks of A-B alternated at regular intervals, and wherein each block of the diblock copolymer has an average molecular weight of from 1,000 g/mol to 500,000 g/mol, and wherein the particles having a polymeric multilayer interference structure include a fixing agent selected from inorganic materials, glycols, and PEGs having a number average molecular weight in a range of from 400 g/mol to 50,000 g/mol.

4. The composition according to claim 1, including at least two different types of particles having a polymeric multilayer interference structure, each particle type having a different transmission spectrum in a wavelength range of from 250 nm to 400 nm.

5. The composition according to claim 1, wherein the particles having a polymeric multilayer interference structure are plate-like.

6. The composition according to claim 1, wherein the particles having a polymeric multilayer interference structure include another optically active material.

7. The composition according to claim 1, wherein the swelling agent is selected from:
water and organic or inorganic saline solutions with a concentration in the range 0.01 M to 5 M;
the following compounds alone, as a mixture, or in aqueous solution: (i) glycerol, PEGs having a number average molecular weight in a range of from 400 g/mol to 50,000 g/mol, mono-, di-, and oligo-saccharides that are soluble in water at at least 1% by weight, sorbitol, propylene glycol, dipropylene glycol, butylene glycol, water-soluble polyols, and water-miscible lower alcohols; (ii) neutralized or non-neutralized solutions of UV screens;

and (iii) polar oils, undecane, tridecane, and solutions of oil soluble organic UV screens in oils.

8. A method of preparing a cosmetic composition according to claim 1, comprising:
   a) bringing a swelling agent into contact with a polymeric multilayer structure having at least two layers comprising an amphiphilic polymer;
   b) fragmenting a film having a polymeric multilayer structure wherein at least two layers comprise an amphiphilic polymer into particles having a polymeric multilayer structure with a largest dimension of less than 100 µm and with a smallest dimension of 100 nm or more;
   c) dispersing the particles with the polymeric multilayer interference structure obtained after carrying out steps a) and b) in a solution containing a fixing agent; and
   d) mixing the particles obtained after carrying out step c) with a cosmetically acceptable medium; wherein step b) is carried out before or after step a).

9. A method of photoprotecting human keratinous materials against solar UV radiation, the method comprising applying the cosmetic composition according to claim 1 to the human keratinous materials.

10. The composition according to claim 1, wherein the at least one dissolved optically active material is selected from the group consisting of a UV screen, a fluorescent agent, a coloring agent and mixtures thereof.

11. The composition according to claim 3, wherein the fatty phase is free of particles having a polymeric multilayer interference structure.

* * * * *